(12) United States Patent
Sanchez et al.

(10) Patent No.: US 9,517,136 B2
(45) Date of Patent: Dec. 13, 2016

(54) VARIABLE-DENSITY IMPLANTS AND RELATED METHODS AND SYSTEMS

(71) Applicant: Amedica Corporation, Salt Lake City, UT (US)

(72) Inventors: James Sanchez, Salt Lake City, UT (US); Paul Sheffield, Queensbury, NY (US); James Ludlow, Salt Lake City, UT (US); Ramaswamy Lakshminarayanan, West Jordan, UT (US)

(73) Assignee: AMEDICA CORPORATION, Salt Lake City, UT (US)

( * ) Notice: Subject to any disclaimer, the term of this patent is extended or adjusted under 35 U.S.C. 154(b) by 116 days.

(21) Appl. No.: 14/217,005

(22) Filed: Mar. 17, 2014

(65) Prior Publication Data

US 2014/0265062 A1    Sep. 18, 2014

Related U.S. Application Data

(60) Provisional application No. 61/786,376, filed on Mar. 15, 2013.

(51) Int. Cl.
| | |
|---|---|
| *A61F 2/34* | (2006.01) |
| *A61F 2/30* | (2006.01) |
| *C04B 35/584* | (2006.01) |
| *C04B 38/00* | (2006.01) |
| *B28B 3/00* | (2006.01) |

(52) U.S. Cl.
CPC ............ *A61F 2/34* (2013.01); *A61F 2/30767* (2013.01); *A61F 2002/30011* (2013.01); *A61F 2002/30769* (2013.01); *A61F 2002/30968* (2013.01); *A61F 2310/00317* (2013.01); *A61F 2310/00604* (2013.01); *A61F 2310/00634* (2013.01)

(58) Field of Classification Search
CPC ................. A61F 2/30767; A61F 2002/30011; A61F 2310/00317; C04B 35/584–35/587; C04B 2235/775; C04B 38/009; C04B 2237/586; B28B 3/003
See application file for complete search history.

(56) References Cited

U.S. PATENT DOCUMENTS

| | | | |
|---|---|---|---|
| 3,505,158 A * | 4/1970 | Murray | .................. C04B 38/00 264/44 |
| 5,244,623 A | 9/1993 | King | |
| 5,250,242 A | 10/1993 | Nishio et al. | |
| 5,686,119 A | 11/1997 | McNaughton, Jr. | |
| 5,714,242 A | 2/1998 | Watanabe et al. | |

(Continued)

*Primary Examiner* — Erin Snelting
(74) *Attorney, Agent, or Firm* — Phillips Ryther & Winchester; Matthew D. Thayne

(57) ABSTRACT

Ceramic orthopedic implants may have one or more dense inner layers and one or more porous outer layers. Methods for manufacturing the implants may include one or more stages during which the dense inner layer(s) are partially compressed. At least one porous outer layer may include coating particles that are present at a surface of one or more inner layer(s) while pressure is applied to attach the coating particles to the inner layer(s) and to further compress one or more of the inner layer(s). Various layers may be formed until an implant, or other device, is formed having the desired density gradient and/or other properties, as disclosed herein.

17 Claims, 43 Drawing Sheets

(56) References Cited

U.S. PATENT DOCUMENTS

| | | | |
|---|---|---|---|
| 5,728,395 A * | 3/1998 | Ohtsuka | A61F 2/28 264/102 |
| 6,149,688 A | 11/2000 | Brosnahan et al. | |
| 6,846,327 B2 | 1/2005 | Khandkar et al. | |
| 7,695,521 B2 | 4/2010 | Ely et al. | |
| 2003/0153984 A1 | 8/2003 | Khandkar et al. | |
| 2004/0175604 A1 | 9/2004 | Ito et al. | |
| 2006/0172073 A1 | 8/2006 | Groza et al. | |
| 2007/0116734 A1 * | 5/2007 | Akash | A61F 2/30 424/423 |
| 2008/0318759 A1 | 12/2008 | Richet et al. | |
| 2011/0251698 A1 * | 10/2011 | Gupta | A61F 2/30767 623/23.56 |

* cited by examiner

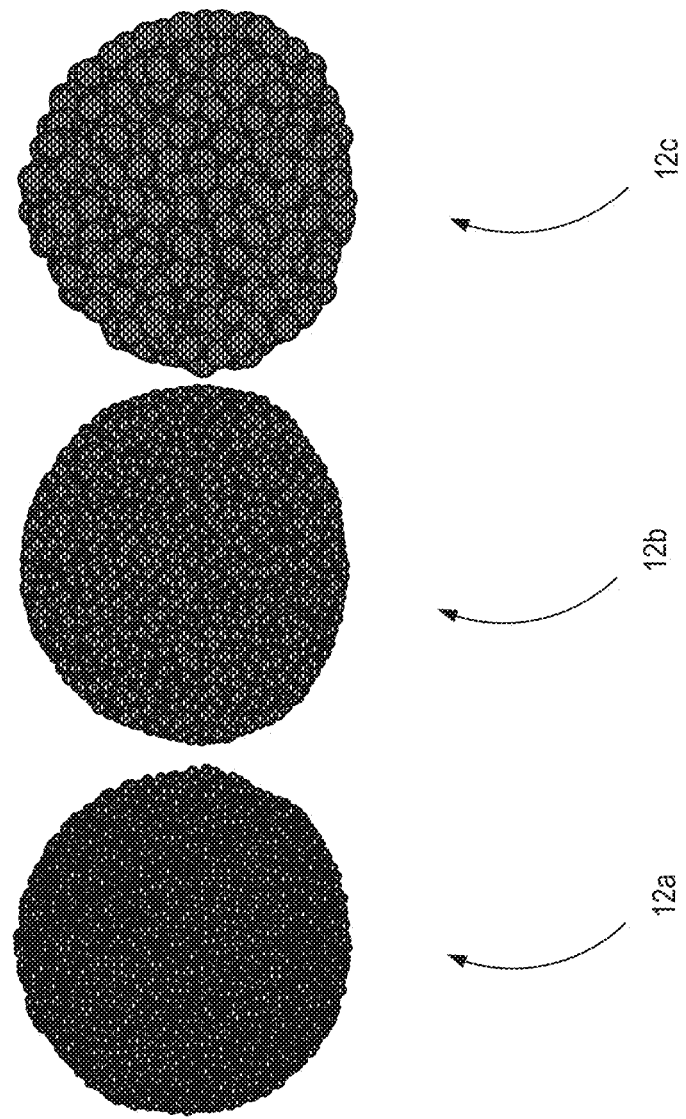

VARIABLE-DENSITY IMPLANTS AND RELATED METHODS AND SYSTEMS

RELATED APPLICATIONS

This application claims the benefit under 35 U.S.C. §119 (e) of U.S. Provisional Patent Application No. 61/786,376 filed Mar. 15, 2013 and titled "VARIABLE-DENSITY IMPLANTS AND RELATED METHODS AND SYSTEMS," which application is incorporated herein by reference in its entirety.

SUMMARY

Disclosed herein are embodiments of ceramic prostheses or other implants comprising one or more dense inner layers and one or more porous outer layers, along with related methods and systems. Methods for manufacturing the implants may comprise one or more stages during which the dense inner layer(s) are partially compressed. At least one porous outer layer may comprise coating particles that may be applied to a surface of one or more inner layer(s) while pressure is applied to attach the coating particles to the inner layer(s) and to further compress one or more of the inner layer(s). Various layers may be formed until an implant, or other device, is formed having the desired density gradient and/or other properties, as disclosed herein.

In a particular example of a method for manufacturing a silicon nitride ceramic hip prosthesis, the method may comprise performing a first isopressing process to form a base portion of a monolithic acetabular cup. The base portion may comprise a silicon nitride ceramic material at a first density.

A second isopressing process may be performed to form coating particles comprising a silicon nitride ceramic material. The coating particles may comprise, for example, silicon nitride chips, silicon nitride coated chips, spherical silicon nitride beads, and/or pore former cores coated with silicon nitride material. Such pore former cores may be configured to form pores in the silicon nitride material upon firing to allow for tuning the porosity of various layers in a ceramic piece.

The coating particles may be combined with the base portion in an isopress mold, after which a third isopressing process is performed on the combined base portion and coating particles to form a first layer of silicon nitride ceramic made up of the coating particles on the base portion. The first layer may comprise a second density less than the first density. The combined base portion and coating particles may be fired to form, for example, a monolithic acetabular cup for a hip prosthesis.

In some embodiments and implementations, a fourth isopressing process may be performed to form a second set of coating particles. The fourth isopressing process may be performed before the third isopressing process. The second set of coating particles may be combined with the base portion and the coating particles, after which a fifth isopressing process may be performed on the combined base portion, coating particles, and second set of coating particles to form a third layer of silicon nitride ceramic made up of the second set of coating particles. The third layer may comprise a third density, less than the second density. Other layers may be applied, as desired, to form a desired density/porosity gradient within the hip prosthesis or other ceramic piece.

In some implementations, the step of performing a third isopressing process may comprise performing the third isopressing process on the base portion, the coating particles, and a second set of coating particles to form the first layer of silicon nitride ceramic made up of the coating particles on the base portion and a second layer of silicon nitride ceramic made up of the second set of coating particles on the first layer. The second layer may comprise a third density less than the second density to provide for a desired density/porosity gradient.

In another specific example of a method for manufacturing a ceramic prosthesis, the method may comprise providing a base for a ceramic prosthesis. The base may comprise a ceramic material comprising at least in part a first density. Coating particles may be formed comprising a ceramic material. The coating particles may be combined with the base in an isopress mold, after which an isopressing process may be performed on the combined base and coating particles to form a first layer of ceramic made up of the coating particles on the base. The first layer may comprise a second density less than the first density. The combined base and coating particles may then be fired to form a ceramic prosthesis.

In some embodiments and implementations, the base may comprise a base for a monolithic acetabular cup of a hip prosthesis.

In some embodiments and implementations, the first layer may comprise a bone ingrowth surface to facilitate secure affixation to natural patient bone. The first layer may be configured to at least generally mimic the characteristics of natural cancellous bone.

In still another example of a method for manufacturing a ceramic biomedical implant, the method may comprise coating a first set of particles with a silicon nitride ceramic powder to form a first set of coated particles. The first set of particles may comprise pore former cores configured to form pores in a silicon nitride ceramic material upon firing. In some embodiments and implementations, the pore former cores may comprise, for example, at least one of polyethylene wax, microcrystalline cellulose, naphthalene, polyethylene glycol, and urea.

A first isopressing process may be performed to form a base of a ceramic biomedical implant. The base may comprise a first density, which may be greater than a density of any other part of the ceramic biomedical implant.

The first set of coated particles may be applied to at least a portion of the base, after which a second isopressing process may be performed on the base with the first set of coated particles to form a first layer having a second density less than the first density. The base and the first set of coated particles may be fired together to form a ceramic biomedical implant. The step of firing the base and the first set of coated particles together may result in the pore former cores evaporating or otherwise forming pores in the first layer.

In some embodiments and implementations, a second set of particles may be coated with a material, such as a silicon nitride ceramic powder, to form a second set of coated particles. The second set of particles may comprise pore former cores configured to form pores in a silicon nitride ceramic material upon firing. The second set of coated particles may be applied to at least a portion of the first layer.

A third isopressing process may be performed on the base with the second set of coated particles to form a second layer having a third density less than the second density. The second set of particles may have a larger maximum diameter than the first set of particles such that the second layer is formed with pores having a larger average volume than the pores in the first layer. This may facilitate providing a desirable density/porosity gradient.

In some embodiments and implementations, one or more of the sets of particles may be sorted by size such that the each respective set of particles comprises only particles having a diameter less than a threshold diameter. This sorting may be done to the pore former particles and/or to the coated particles.

In some embodiments and implementations, the base portion may comprise a silicon nitride ceramic material.

In some embodiments and implementations, a third isopressing process may be performed to form the first set of coating particles. The step of performing a third isopressing process may be performed before the step of performing a second isopressing process.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 35 is a perspective view of the three embodiments of multi-layer ceramic parts of FIG. 34, wherein the parts have been fired;

DETAILED DESCRIPTION

Figure 1A:
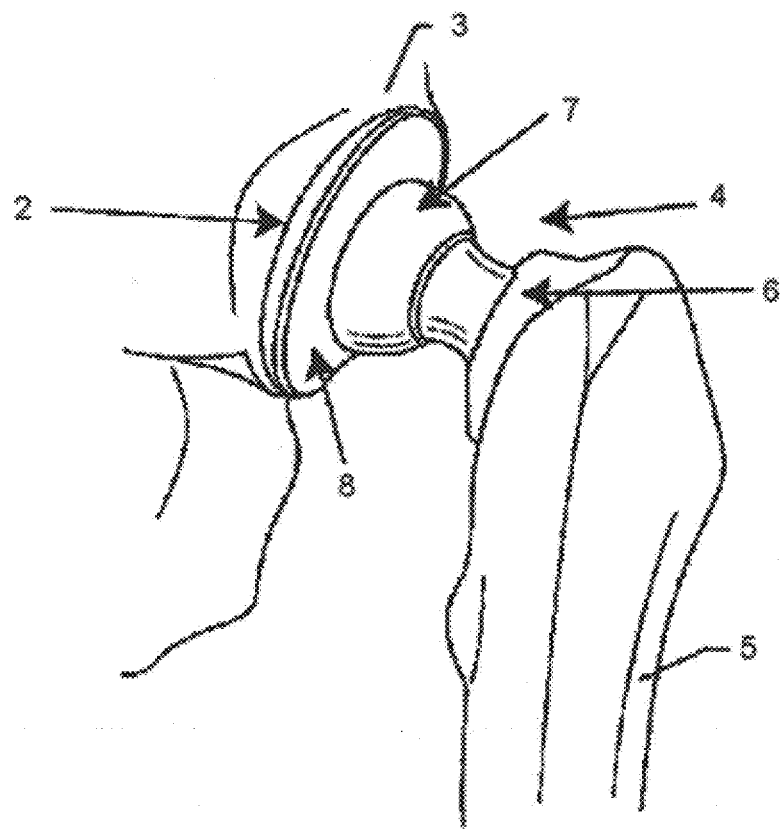
FIG. 1A is a partial perspective view of a prior art hip prosthesis installed in an acetabulum of a patient.

Certain embodiments disclosed herein relate generally to ceramic prosthetic devices that have varying densities, as well as methods for forming the same. For example, some embodiments comprise a hip joint prosthesis that includes an outer portion having a greater porosity, or lower density, than an inner portion thereof. The hip joint prosthesis may be, for example, an acetabular cup that is configured to be fixedly joined with a pelvis (e.g., at an acetabulum socket) at one side thereof, and to be rotationally joined with a ball-shaped joint at an opposite side thereof. The side that is to be fixedly joined to the pelvis may be more porous, or less dense, than the opposite side, such that bone can readily grow into or otherwise fuse with the less dense portion of the prosthesis, and the denser portion of the prosthesis can be wear-resistant. Those of ordinary skill in the art, however, may appreciate that the principles of the invention may have applicability in a wide variety of other implants, medical devices, or other devices.

Embodiments of the ceramic prostheses can be formed as a unitary or monolithic part, which may also be referred to as a "monoblock" cup. In some embodiments, a base portion, or inner cup, is formed by partially compressing ceramic powder into a desired shape. Smaller surface particles, or coating particles, which also can be formed with the ceramic powder, can be fabricated separately from the inner cup. In some instances, the coating particles may also be compressed and, in further instances, may be compressed under greater pressure than that used in forming the inner cup. The inner cup and the coating particles can be positioned adjacent to each other, and an additional stage of compression can permanently join the coating particles to the inner cup, thereby yielding a monoblock cup. The joining stage can occur while both the inner cup and the coating particles are in a green state. After the monoblock cup has been formed, it may be fired and/or otherwise hardened into a finalized form.

Although the term "base" is primarily used herein to refer to an inner cup of a hip prosthesis, those of ordinary skill in the art will appreciate that a wide variety of other "bases" for other prostheses and/or biomedical implants may be used in conjunction with one or more of the inventive features, aspects, or steps disclosed herein. For example, in some embodiments, the "base" may comprise a core portion of a dental implant, in which case outer less dense layers may be applied, using the principles disclosed herein, to allow for integration with bone in a patient's oral cavity.

A variety of configurations for the coating particles are possible, and these particles may be formed via a variety of different methods. Accordingly, multiple different configurations for the outer surface of the monoblock cup are possible. Different methods disclosed herein with respect to formation of the coating particles and the joining thereof to an inner cup may advantageously be optimized to achieve a monoblock cup having desired properties. Such properties may include, for example, optimal bone ingrowth or bone attachment at one side and optimal density, hardness, and/or wear resistance at another side thereof. Methods disclosed herein for joining the coating particles with the inner cup may also advantageously create a robust monoblock cup, one in which the layers having different densities are securely, or even integrally, attached to each other. One or more of the foregoing advantages, as well as others, will be evident from the following discussion.

FIG. 1A illustrates a traditional hip prosthesis construction for repairing or replacing the natural anatomical ball-and-socket human hip joint. More specifically, FIG. 1A shows an acetabular cup 2 seated and/or affixed within the patient's natural acetabulum or socket 3. The acetabular cup 2 may operate in conjunction with a femoral component 4, which may be seated within a resected upper end of the patient's femur bone 5 and/or an upwardly protruding femoral neck 6, and can include a ball-shaped femoral head 7 mounted or otherwise formed on an upper end of the neck 6. The femoral component 4 may also include an elongated stem (not shown). A generally cup-shaped bearing insert 8 formed typically from a polymer-based material such as a high density or high molecular weight polyethylene (PE) or the like is normally fitted between the acetabular cup 2 and the femoral head 7 to accommodate smooth articulation between these components. However, as noted in U.S. Pat. No. 7,695,521, premature prosthesis failure has been attributed to the generation and accumulation of polymer-based wear debris associated with the bearing insert 8. A further drawback to the use of polymer-based inserts can be the higher thickness of the construct, restricting its application to larger bone patients capable of receiving the larger sizes, and thus preventing the use of larger diameter heads in smaller bone patients.

Certain embodiments can overcome one or more of the foregoing drawbacks of the prior art. For example, various methods described herein can be used to form any of the advantageous acetabular cups disclosed in U.S. Pat. No. 7,695,521. The contents of U.S. Pat. No. 7,695,521 are hereby incorporated herein by reference.

As discussed in U.S. Pat. No. 7,695,521, an improved hip joint prosthesis can be constructed in any one of a plurality of alternative preferred forms, to include improved implantable and biocompatible materials designed for achieving ultra-low wear as a consequence of component articulation over an extended service life or duty cycle, using a ceramic-on-ceramic or a ceramic-on-metal articulatory interface, and omitting use of the traditional polymer-based bearing insert.

Figure 1B:
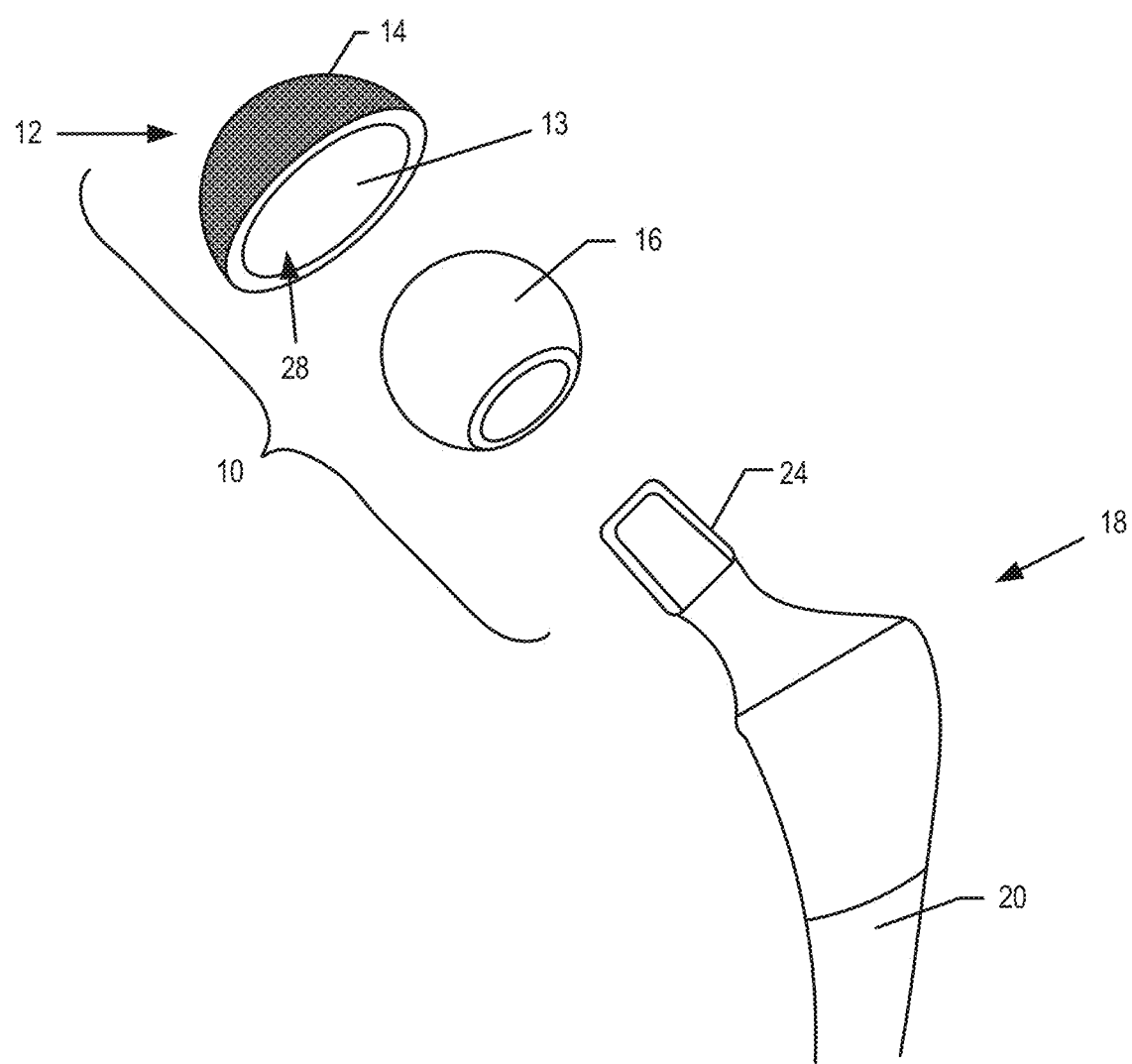
FIG. 1B is an exploded perspective view of an embodiment of a hip prosthesis that includes an acetabular cup.

One such illustrative improved hip prosthesis is depicted in FIG. 1B, and is identified by the reference numeral 10. The prosthesis 10 includes an acetabular cup 12 constructed from a relatively hard and high strength ceramic material which may also incorporate a relatively porous ceramic bone ingrowth surface 14 for secure affixation to patient bone. The cup 12 is designed for articulation with other prosthesis components such as a ball-shaped femoral head component 16, which may be constructed from a hard and high strength material, such as a compatible and, in some instances, identical ceramic material, a biocompatible metal material, or any other suitable material. The resultant ceramic-on-ceramic or ceramic-on-metal articulatory interface can beneficially exhibit ultra-low wear over an extended service life, and may eliminate traditional polymer-based bearing inserts and wear debris problems associated therewith. The hip joint prosthesis 10 can include improved implantable and biocompatible materials designed for achieving a thinner overall acetabular cup diameter, and as a consequence, can allow for the use of larger diameter heads on smaller bone patients than otherwise possible.

The prosthesis 10 can be of either a unipolar or bipolar form. For example, in some embodiments, the prosthesis 10 can be of a unipolar form, and may include a prosthetic acetabular cup 12 that is configured to receive and permit a natural femoral head to articulate therein. In other embodiments, the prosthesis 10 can be of a bipolar form, such that the prosthetic acetabular cup 12 is used in conjunction with a prosthetic femoral head.

In the illustrated embodiment, the acetabular cup 12 has a generally cup-shaped or shell-shaped geometry defining a downwardly open cavity 28 that defines a portion of a sphere. In the illustrated embodiment, the cavity 28 is substantially hemispherical. The shell-shaped acetabular cup 12 can have a size selected for substantially conformal seated reception into the generally complementarily shaped acetabulum or socket 3 (see FIG. 1A), which may be surgically prepared as by removal of accumulated calcium deposits or other procedures known in the art. The acetabular cup 12 can be formed from a relatively high strength and high toughness or high hardness ceramic material defining a substantially spherically shaped substrate, or inner cup 13, lining the cavity 28 to define an articulation surface for receiving and articulating against the ball-shaped femoral head 16. In the illustrated embodiment, the femoral head 16 is prosthetic, such that the illustrated prosthesis 10 is of a bipolar variety. More generally, the femoral head 16 is part of a prosthetic femoral component 18, which may be seated within a resected upper end of the patient's femur bone and may include an elongated stem 20. The femoral component 18 can include a neck 24 to which the femoral head 16 is mounted.

In certain embodiments, the ceramic material used for constructing the ceramic acetabular cup 12 has a high flexural strength and high fracture toughness. For example, the ceramic material can comprise a doped silicon nitride ($Si_3N_4$) having relatively high hardness, tensile strength, elastic modulus, lubricity, and fracture toughness properties. Examples of suitable silicon nitride materials are described, for example, in U.S. Patent Application Publication No. 2003/0153984, which is incorporated by reference herein. In some embodiments, the doped silicon nitride ceramic material has a relatively high flexural strength, e.g., greater than about 700 Mega-Pascal (MPa), and a relatively high fracture toughness, e.g., greater than about 7 Mega-Pascal root meter (MPa $m^{0.5}$). This high strength and high toughness doped silicon nitride ceramic can achieve ultra-low wear over an extended service life, with dramatically reduced risk of brittle fracture. Powders of silicon nitride ($Si_3N_4$) and dopants, such as alumina ($Al_2O_3$), yttria ($Y_2O_3$), magnesium oxide, and strontium oxide, can be processed in a conventional manner to form a doped composition of silicon nitride. The dopant amount may be optimized to achieve the highest density and mechanical properties, in some instances. In further embodiments, the biocompatible ceramic has a flexural strength greater than about 800 Mega-Pascal (MPa) and a toughness greater than about 9 Mega-Pascal root meter (MPa $m^{0.5}$). Flexural strength can be measured on standard 3-point bend specimens per American Society for Testing of Metals (ASTM) protocol method C-1161, and fracture toughness can be measured using single edge notched beam specimens per ASTM protocol method E399. Other ceramics having other properties may also be used in some embodiments, such as zirconia toughened alumina, zirconia, etc.

In certain embodiments, a high strength and high toughness ceramic material is used to form the inner cup 13 of the monoblock cup 12. The inner cup 13 may have a relatively low porosity, and thus exhibit high density and high structural integrity generally consistent with, and generally mimicking the characteristics of, natural cortical bone lined with smooth lubricious articular cartilage. One or more of the surface coatings, layers, or linings 14 formed at the outer surface of the inner cup 13 can exhibit a comparatively greater or higher porosity that is generally consistent with and generally mimics the characteristics of natural cancellous bone. As a result, the higher porosity surface coating(s) or lining(s) 14 can provide an effective bone ingrowth surface for achieving secure and stable bone ingrowth affixation of the ceramic acetabular cup 12 within the patient's acetabulum and the high density/low porosity portions of the implant, such as inner cup 13 and femoral head 16, can provide smooth, strong, and tough articulation surfaces.

The specific material used for the bone ingrowth surface layer, coating, or lining 14 may vary. In some embodiments, the porous material comprises a ceramic porous ingrowth surface material. For example, suitable materials are disclosed in U.S. Pat. No. 6,846,327, which is incorporated by reference herein. U.S. Pat. No. 6,846,327 discloses a ceramic bone graft component having relatively high flexural strength and relatively high toughness properties, yet defining first and second regions of comparatively lower and higher porosity to respectively mimic natural cortical and cancellous bone structures. These regions of different porosity may be unitarily constructed or otherwise integrated into a common or monolithic ceramic component having a variable porosity gradient. In some embodiments, the ceramic cup 12 has a porosity gradient ranging from about 2% to about 80% by volume, with the higher porosity region having a porosity in the range of from about 30% to about 80% by volume, and with overall pore sizes ranging from about 10 microns to about 500 microns. Other arrangements are described further below. In use, the relatively low porosity region of the inner cup 13 can provide a dense and hard structure with high structural strength and integrity, whereas the higher porosity or less dense region 14 is suitable for bone ingrowth to achieve secure and stable implant affixation.

U.S. Pat. No. 6,846,327 also discloses a suitable alumina-zirconia ceramic material having a zirconia composition of about 10% to about 20% by volume, with either yttria stabilized zirconia (about 2.5 to about 5 mol % yttria in zirconia) or ceria stabilized zirconia (about 2.5 to about 15 mol % ceria in zirconia) for the zirconia phase. The resultant ceramic material exhibits a highly desirable combination of high flexural strength (e.g., greater than about 500 MPa) and high fracture toughness (e.g., greater than about 5 MPa $m^{0.5}$). Such alumina-zirconia based ceramic material may be employed in one or more portions, such as one or more layers, of the acetabular cup 12.

The femoral head 16 is sized and shaped for articulatory reception within the acetabular cup cavity 28. In some embodiments, such as the embodiment shown in FIG. 1B, the femoral head 16 is constructed from a ceramic material that is compatible with the ceramic cup material. For example, the femoral head 16 can comprise a matching or identical high strength and high toughness ceramic material corresponding with the acetabular cup material, such as that disclosed in U.S. Patent Application Publication No. 2003/0153984. In other embodiments, the femoral head 16 may be constructed from a biocompatible metal material, such as, for example, a cobalt chrome alloy such as that disclosed in U.S. Patent Application Publication No. 2003/0153984. In still other embodiments, the acetabular cup component 12, which is also referred to herein as a monoblock cup 12, may be used for articulatory engagement with the natural ball-shaped femoral head at the upper end of the patient's femur, or with an appropriately capped natural femoral head.

Figure 2:
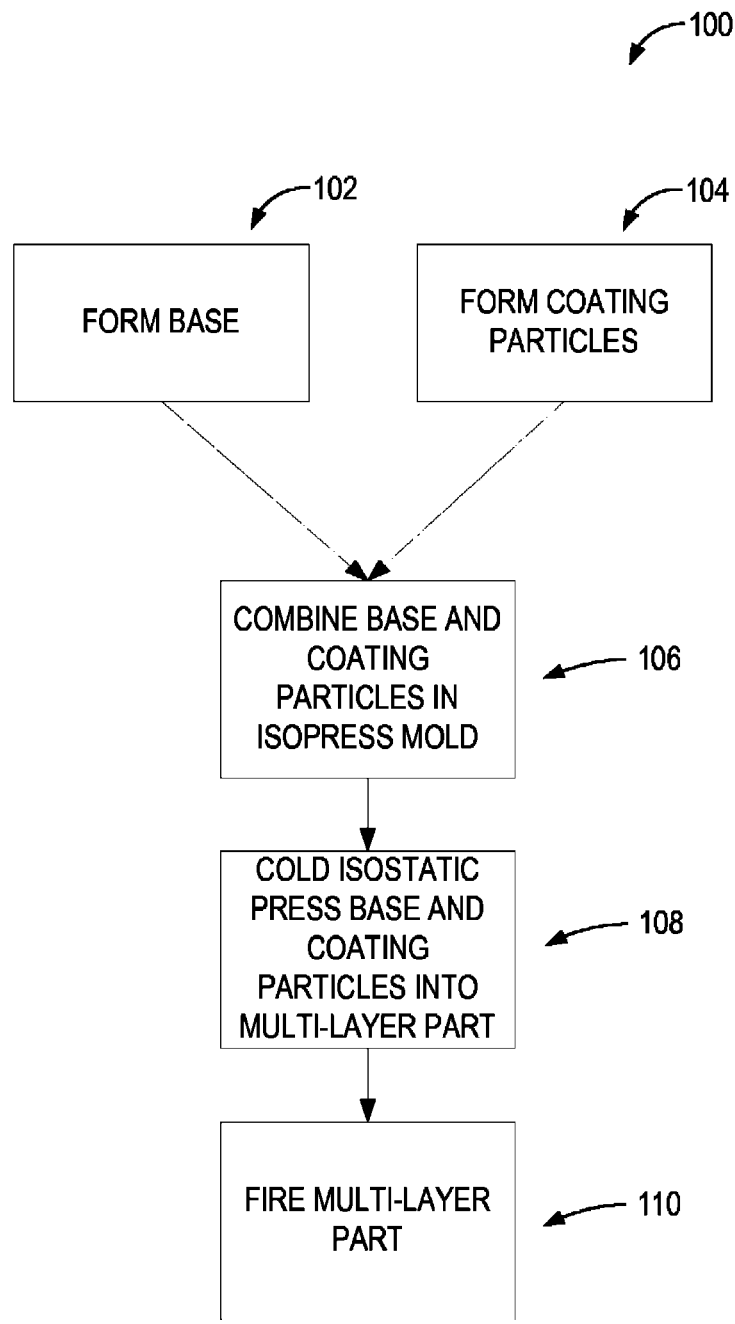
FIG. 2 is a flow chart that depicts an illustrative method for forming a multi-layer ceramic part, such as the acetabular cup of FIG. 1B, that has a variable density.
Figure 5:
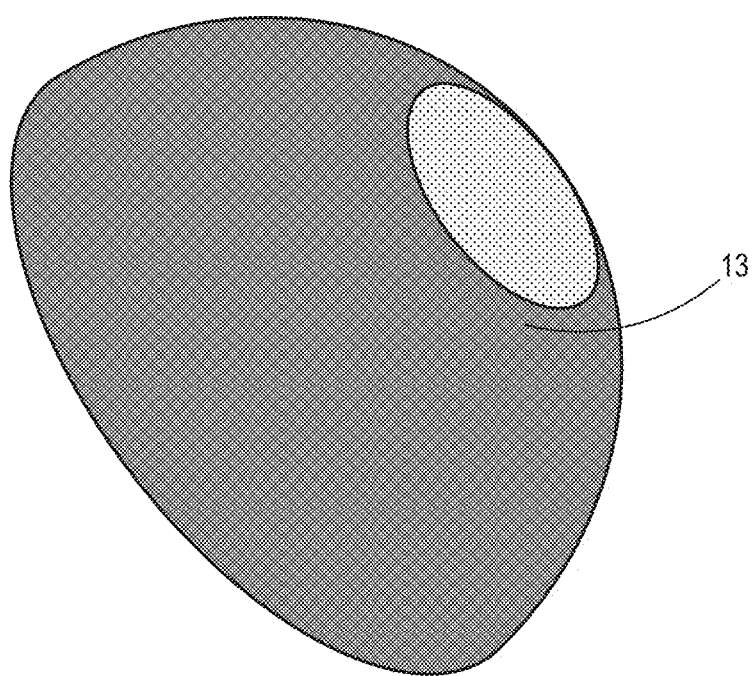
FIG. 5 is a perspective view of an embodiment of a base piece that is in a green state and that has been formed in accordance with the method of FIG. 3.

FIG. 2 depicts an illustrative method 100 for manufacturing a multi-layer ceramic part, such as the monoblock cup 12 discussed above. At stage 102, a base is formed. The base can comprise any suitable base component to which coating particles may be attached. For example, the base can comprise the inner cup 13 discussed above (see FIG. 1B). An illustrative example of a base 13 is shown in FIG. 5. As further discussed below, in some embodiments, forming the base 13 comprises compressing ceramic powder into a solid part, such as via cold isostatic pressing (CIP). At the completion of stage 102, the base can be in a green state, and may readily be combined with coating particles to form a monolithic structure therewith, as discussed further below.

At stage 104, coating particles are formed. An example of coating particles 179 is provided in FIG. 8. The coating particles can be configured for joining to the base, and may be configured to form a portion of the multi-layer ceramic part that is less dense than the base. As further discussed below, in some embodiments, the coating particles can be formed without compressing the coating particles (e.g., without CIP), whereas in other embodiments, CIP is used in forming the coating particles. In various embodiments, the stages 102 and 104 may be performed in series (in either order) or in parallel. In some embodiments, at the completion of stage 104, the coating particles may include ceramic material that is in a powder state, such that the ceramic material has not been compacted into one or more unified structures, as discussed further below (e.g., with respect to the methods in FIGS. 6 and 7). In other embodiments, at the completion of stage 104, the coating particles may each comprise compacted ceramic material, as discussed further below (e.g., with respect to the methods in FIGS. 14, 22, 23, 29, and 30). In either case, the coating particles may be in a green, or unfired, state at the completion of stage 104, and may readily be joined with the base.

At stage 106, the base and the coating particles are combined in an isopress mold. The base and the coating particles may be introduced into the isopress mold at the same time or at approximately the same time. In other embodiments, the base may be formed within the isopress mold at stage 102 and may remain within the isopress mold at stage 106 while the coating particles are added to the isopress mold.

At stage 108, the base and coating particles are cold isostatic pressed so as to be joined to each other in a multi-layer part. For example, the isopress mold may be sealed at or after stage 106, and pressure may be applied thereto at stage 108. At the completion of stage 108, the multi-layer part can be in a green state. As is discussed in greater detail elsewhere, many different layers, each of varying density and/or composition, may be provided as desired in order to provide an implant or other ceramic product of the desired density gradient and/or of other desired properties. At stage 110, the multi-layer part can be fired or finalized for use in any other suitable manner.

The method 100 is described in broad and general stages. As will be evident from the following discussion, many different processes and sub-processes for the various stages of the method 100 are contemplated.

Figure 3:
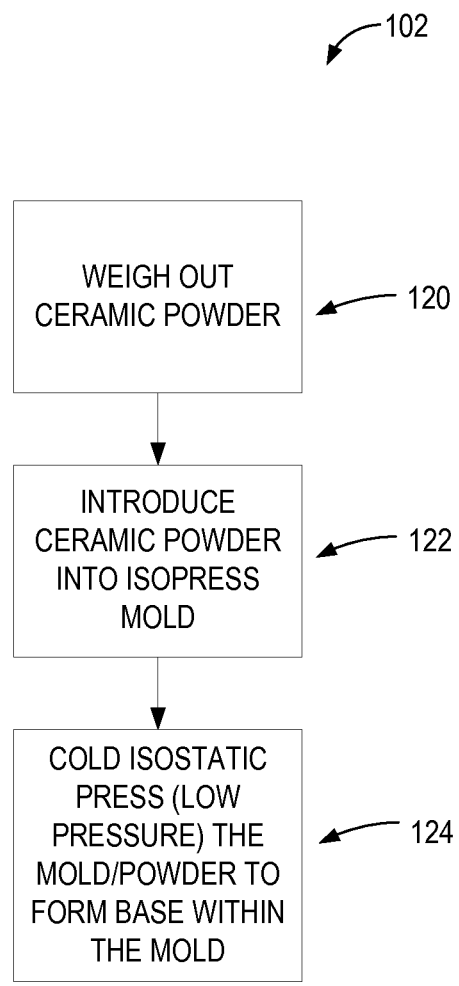
FIG. 3 is a flow chart that depicts an illustrative method for forming a base portion of the multi-layer ceramic part of FIG. 2.

For example, FIG. 3 depicts an illustrative example of the stage 102 of the method 100. The stage 102, which may also be described as a method 102, can be used to form the base or inner cup 13. It is noted that the inner cup 13 may also be referred to as the cortical portion of the monoblock cup 12, as this portion of the cup 12 may desirably resemble natural cortical bone lined with smooth lubricious articular cartilage, as discussed above. At stage 120, a desired amount of ceramic powder is weighed out. As mentioned above, any suitable ceramic powder may be used. The ceramic powder may be selected based on the desired properties of the inner cup 13, such as those discussed above. In some embodiments, the ceramic powder comprises $Si_3N_4$.

At stage 122, the ceramic powder is introduced into an isopress mold. The mold may be of any suitable variety, and can be configured to yield the desired shape and configuration of the base. In various embodiments, the mold can comprise silicone and/or urethane. In some embodiments, the isopress mold comprises a resilient material such that it can return, or substantially return, to an original shape after having been compressed via an isostatic pressing procedure, as discussed further below.

The ceramic powder can be tightly packed into the isopress mold. For example, in some embodiments, a vibration plate or other vibration mechanism is used to tightly pack the ceramic powder within the isopress mold.

At stage 124, CIP of the mold and powder compacts the powder into a desired base shape, although in some embodiments, the base is not fully compacted into its final size (when in the green state) at this stage. In particular, in some embodiments, at stage 124, the powder is compacted into an intermediate, or partially compacted, base. CIP can be used to compress the base further at a later stage in a process for creating the multi-layer part (e.g., as discussed further below with respect to FIG. 9). In various embodiments, pressures used for the CIP at stage 124 are within a range of from about 1,000 psi to about 10,000 psi; from about 2,500 psi to about 7,500 psi, from about 3,000 psi to about 6,000 psi, or from about 4,000 psi to about 5,000 psi, or the pressures are no greater than about 4,000; 4,500; 5,000; 5,500; 6,000; 6,500; 7,000; 7,500; 8,000; 8,500; 9,000; 9,500; or 10,000 psi. In some embodiments, a pressure of about 4,500 psi is used. In various embodiments, a cold isostatic press that is rated at approximately 30,000 psi can be used for the CIP procedure.

In other embodiments, the pressures used for the CIP stage, or other stages involved in the process of forming a variable density implant or other device, may be within a range from about 5,000 psi to about 50,000 psi. Indeed, higher pressures may be needed in some steps of some implementations in order to provide a better fine tuning of the densities in one or more layers/regions of the device.

Figure 4:
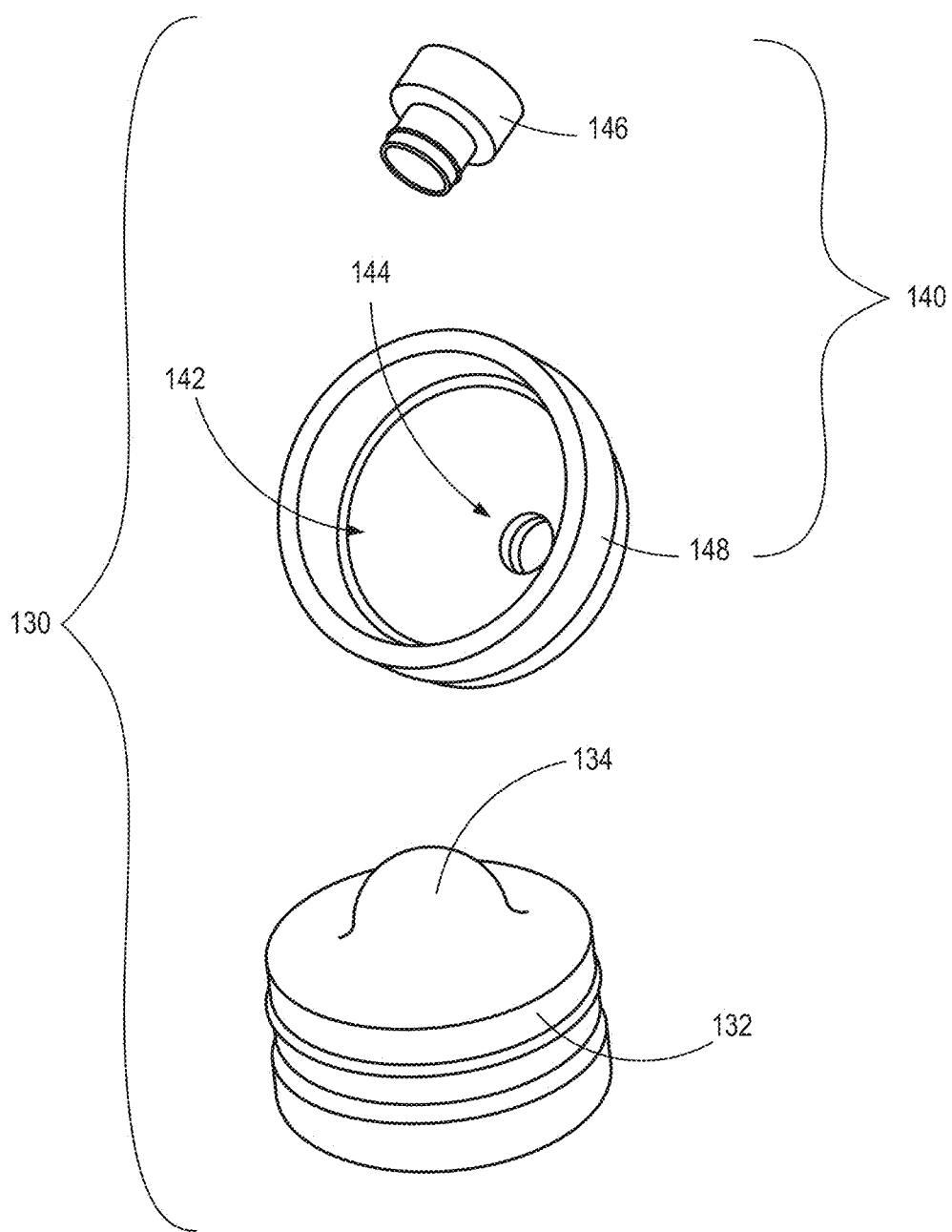
FIG. 4 is a perspective view of an embodiment of isopress tooling that is configured for use in forming a multi-layer ceramic part, such as the acetabular cup of FIG. 1B.

FIG. 4 depicts an illustrative embodiment of CIP tooling 130 that is suitable for use with the method 102. The tooling 130 can include a base, support, or seat 132 that may be substantially incompressible at pressures generally used in CIP. For example, in some embodiments, the seat 132 comprises stainless steel. In the illustrated embodiment, the seat 132 defines a protrusion 134, which is shaped substantially as a hemisphere. The protrusion 134 can act as a negative to form the cavity 28 of the monoblock cup 12, which is described above. Accordingly, the protrusion 134 can be sized and shaped to achieve the desired dimensions of the cavity 28.

The tooling 130 can further comprise an isopress mold 140, which may include a fitting 148 that is configured to be joined with the seat 132 and a plug 146. The fitting 148 can define a cavity 142 and a port 144 through which material can be introduced into the cavity 142. The plug 146 can be configured to be selectively attached to the fitting 148 so as to close the port 144. In the illustrated embodiment, the port 144 and the plug 146 are complementarily threaded for this purpose.

The isopress mold 140 can comprise any suitable material, such as those discussed above. Accordingly, the mold 140 can be configured to contract (e.g., substantially uniformly) toward the seat 132 during application of pressure at an exterior thereof, and to retract from the seat 132 to an original orientation upon removal of the pressure.

FIG. 5 is a perspective view of an embodiment of a partially formed or partially compacted base 13 that has been formed in accordance with the method 102. Tooling similar to the tooling 130 was used to create the partially compacted base 13. However, the tooling was shaped somewhat differently. The tooling 130 is configured to create a substantially hemispherical base 13, such as that depicted in FIG. 1B (see also FIG. 39). In contrast, the base 13 in FIG. 5 defines a greater portion of a sphere. Additionally, a cavity 28 defined by the base 13 is not hemispherical (see FIG. 10).

Figure 6:
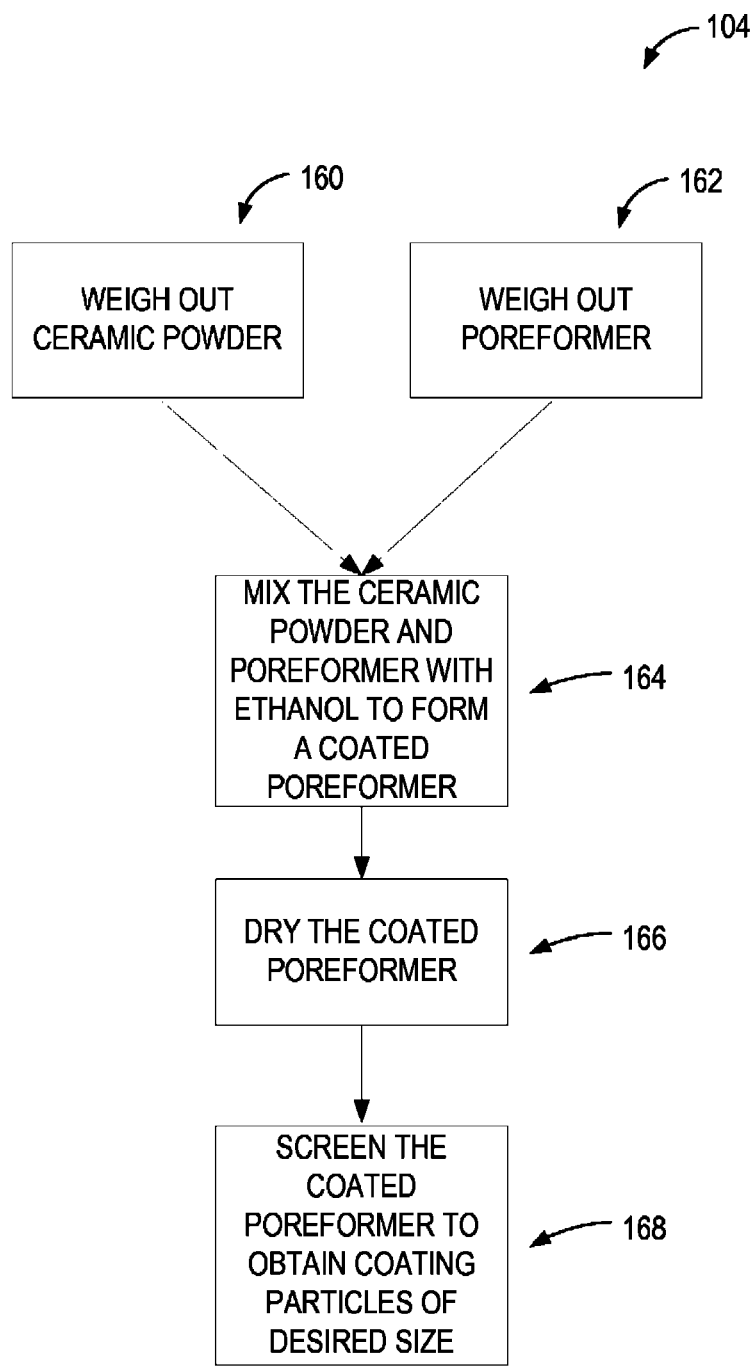
FIG. 6 is a flow chart that depicts an illustrative method for forming coating particles that can be mounted to a base piece, such as that shown in FIG. 5.

FIG. 6 depicts an illustrative example of the stage 104 of the method 100, which may itself be referred to as a method 104. The stage or method 104 can be used to form coating particles that are in a green state. At stage 160, a desired amount of ceramic powder is weighed out. As mentioned above, any suitable ceramic powder may be used. The ceramic powder may be selected based on the desired properties of the porous, or relatively less dense, region 14 of the monoblock cup 12. In some embodiments, the ceramic powder comprises $Si_3N_4$.

At stage 162, a desired amount of pore former is weighed out. The term "pore former" is a broad term used in its ordinary sense and includes any suitable material that can be used to form pores in a ceramic material. In many embodiments, the pore former comprises an organic material that is volatile at firing temperatures such that, after firing of a monoblock cup, pores are formed within the less dense region 14 at those positions where the pore former material was located. For example, in various embodiments, the pore former can comprise one or more of polyethylene wax, microcrystalline cellulose, naphthalene, polyethylene glycol, and urea. Any other suitable material is contemplated. In various embodiments, the pore former material may be formed in the shape of beads (e.g., spheres), flakes, or chips. In other or further embodiments, the pore former particles may have a maximum diameter of from about 50 microns to about 2,000 microns, from about 100 microns to about 1,500 microns, from about 200 microns to about 1,250 microns, from about 300 microns to about 1,000 microns, from about 500 microns to about 750 microns, from about 50 to about 500 microns, from about 500 microns to about 1,000 microns, or from about 1,000 microns to about 2,000 microns, or the pore former particles may have a maximum diameter of no less than about 50, 100, 150, 200, 250, 300, 350, 500, 750, 1,000, or 1,500 microns, or no greater than about 50, 100, 150, 200, 250, 300, 350, 500, 750, 1,000, 1,500, or 2,000 microns.

At stage 164, the ceramic powder and pore former material are mixed with each other such that the pore former is coated with the ceramic powder. Shaking or other agitation may be used to evenly or substantially evenly coat the pore former. A quantity of ethanol or other suitable solvent may also be included in the mixture to facilitate the coating of the pore former. Examples of other potentially suitable polymers include, for example, alcohols, such as isopropyl alcohol, acetone, or another low-viscosity organic solvent.

At stage 166, the coated pore former is permitted to dry. For example, the ethanol or other solvent is permitted to evaporate such that the ceramic powder remains firmly attached to the pore former.

At stage 168, the ceramic-coated pore former and excess ceramic powder are screened, which removes excess ceramic powder from the pore former material. The screen may also be used to obtain coating particles of a desired size. The term "coating particles" is used herein to describe the particles that will be joined to the partially compacted base. Accordingly, in the instant case, the coating particles comprise pore former particles that are coated with ceramic powder. Other coating particle configurations are also possible, as discussed further below.

Figure 7:
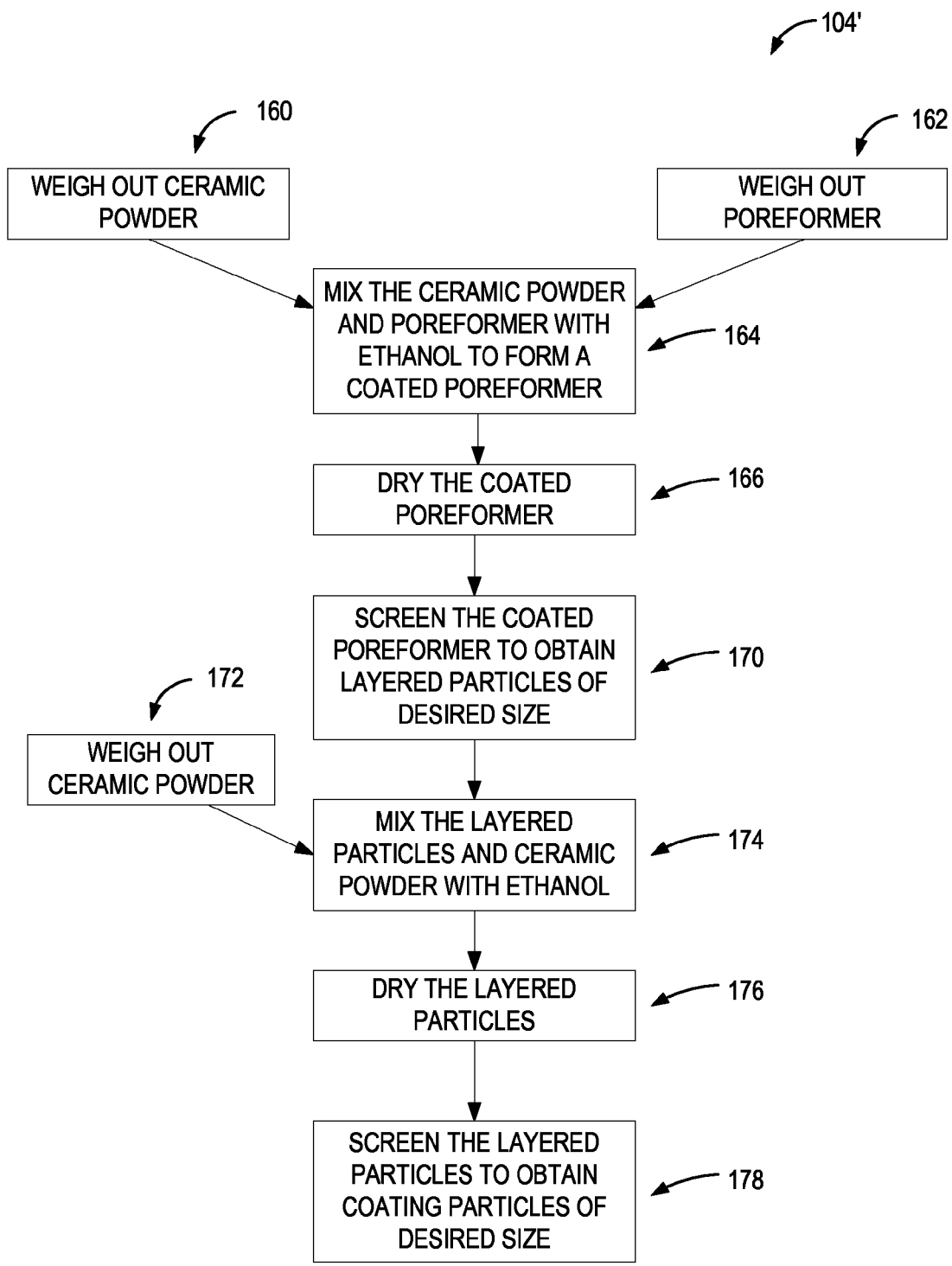
FIG. 7 is a flow chart that depicts another illustrative method for forming coating particles that can be mounted to a base piece, such as that shown in FIG. 5.

FIG. 7 illustrates another method 104' that can be used to create coating particles. Stages 160, 162, 164, and 166 may be identical to those discussed above with respect to the method 104. At stage 170, however, the ceramic-coated pore former particles are referred to merely as "layered particles" rather than "coating particles," since additional alteration to the particles takes place before they are used to "coat" at least a portion of the base. The term "layered" within the phrase "layered particles" refers specifically to the particles themselves, as these particles include two primary layers—namely, a pore former core and ceramic powder coating. In contrast, the term "coating particles" is a broader term that is used throughout the present application to refer to particles that are joined, or are prepared to be joined, to a base portion, whether directly or indirectly. For example, the term can refer to particles that are joined, or have been prepared for joining, to an inner cup 13, whether the particles are joined in direct or abutting contact with the inner cup 13, or whether the particles are not joined with the inner cup 13 directly, but are instead attached to one or more additional coating particles that are themselves directly attached to the inner cup 13. Coating particles can have a variety of forms. For example, the coating particles may include "layered particles," such as those just described (i.e., those having a pore former core and a ceramic powder coating). In other instances, coating particles can include particles that are not layered or that have a substantially uniform composition. For example, in some embodiments, the coating particles can comprise pieces of compressed ceramic powder that do not include a pore former material. Examples of such coating particles are discussed further below (e.g., the ceramic chips of FIG. 16A and the ceramic beads of FIG. 32).

At stage 174, the layered particles are combined with additional ceramic powder, which is weighed out to the desired amount at stage 172. Ethanol or other suitable solvent may be used to assist in the further coating of the layered particles. Shaking or other suitable agitation of the components may also assist in the coating procedure. At stage 176, the augmented layered particles are permitted to dry. At stage 178, the layered particles and excess ceramic powder are screened and coating particles of a desired minimum size are obtained. Thus, the method 104' can yield coating particles that have a greater amount of ceramic powder adhered thereto.

Figure 8:
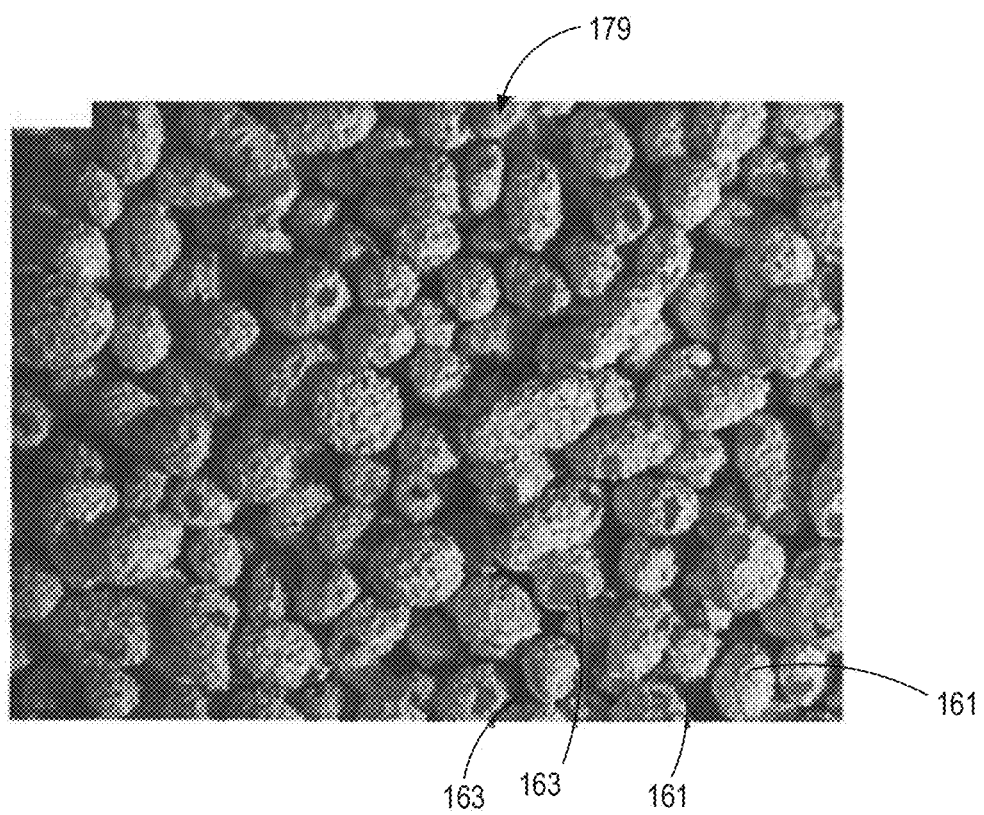
FIG. 8 is a perspective view of an embodiment of coating particles that are in a green state and have been formed in accordance with the method of FIG. 7, wherein the scale depicted in the insert at the upper left-hand corner of the photograph defines a length of 1000 μm.

FIG. 8 is a perspective view of coating particles 179 that have been gathered at stage 178 of method 104'. As can be seen, each coating particle 179 includes a pore former core 163 that is coated with ceramic powder 161. In the illustrated embodiment, the performer cores 163 are substantially ovoid beads. Other shapes and configurations are possible.

In one illustrative example, the coating particles are formed according to the following procedure. The details provided with respect to this procedure are not intended to limit the present disclosure generally, although inventive concepts and independently claimable subject matter may be present within such details. Approximately 22.4 grams of $Si_3N_4$ are weighed out, and approximately 5.6 grams of a wax pore former are weighed out. Both components are introduced into a plastic bottle. Approximately 7.6 grams of ethanol are introduced into the bottle and the bottle is then closed. The bottle is shaken (e.g., by hand or otherwise) for approximately 1 minute. The mixed contents are then poured into a weigh boat and permitted to dry (e.g., overnight). The approximately 28-gram mixture is screened via a 425 micron sieve. The screening rids the coated pore former of excess $Si_3N_4$ powder that did not adhere to the pore former. The screened pore former/$Si_3N_4$ combination is then combined with another 18 grams of $Si_3N_4$ powder in a plastic bottle. Approximately 7.6 grams of ethanol are introduced into the bottle and the bottle is then closed. The bottle is shaken (e.g., by hand or otherwise) for approximately 1 minute. The mixed contents are then poured into a weigh boat and are permitted to dry (e.g., overnight). The contents are then screened via a 425 micron sieve (e.g., via a Ro-Tap® stackable test sieve shaker available from W.S. Tyler of Mentor, Ohio).

Figure 9:
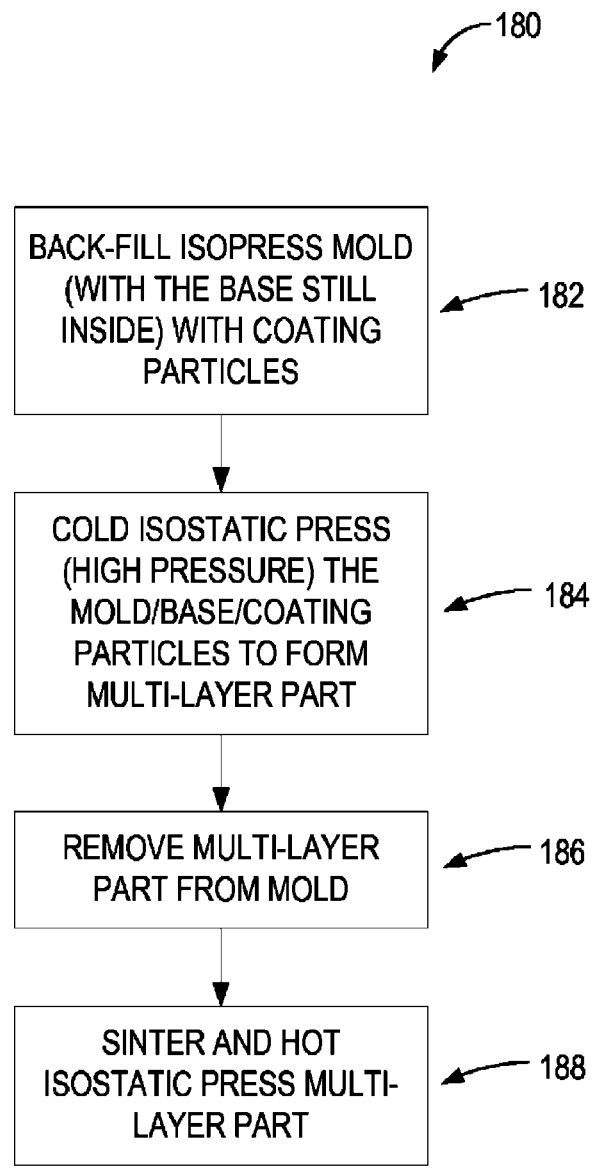
FIG. 9 is a flow chart that depicts an illustrative method of joining coating particles, such as those shown in FIG. 8, with a base piece, such as that shown in FIG. 5.

FIG. 9 depicts a method 180 by which the base 13 is combined with coating particles (e.g., the coating particles 179) to form one or more outer layers 14. The base 13 and the outer layer(s) 14 thus form an integral or monolithic unit or, in the illustrated embodiment, a monoblock cup. The method 180 provides an example of carrying out the stages 106, 108, and 110 of the method 100 discussed above.

At stage 182, the isopress mold is back-filled with coating particles. In particular, the partially-compacted base 13 can be left within the isopress mold after it has been compressed during an initial CIP phase. For example, after the completion of stage 124 of method 102 (see FIG. 3), the base 13 can be left within the mold and the tooling can be left in place. Removal of pressure from the isopress mold, however, can allow the isopress mold (e.g., the mold 140 of FIG. 4) to return to its original orientation, which can leave open headspace in the cavity 142 between the outer surface of the base 13 and the inner surface of the mold fitting 148. In the illustrated embodiment, the plug 146 can be removed from the port 144, and the coating particles 179 (FIG. 8) can be introduced into the open headspace via the port 144. In some embodiments, a vibratory plate or other vibration mechanism is used to tightly pack the coating particles 179 into the isopress mold 140. Once the coating particles 179 are in place, the plug 146 can be returned to close the port 144.

At stage 184, cold isostatic pressing of the mold, the coating particles, and the base tightly secures the coating particles to the base as these components are compacted. In various embodiments, pressures used for the CIP at stage 184 are within a range of from about 20,000 psi to about 66,000 psi; from about 25,000 psi to about 50,000 psi, or from about 30,000 psi to about 40,000 psi; the pressures are no greater than about 25,000; 30,000; 35,000; 40,000; 45,000; or 50,000 psi; or the pressures are no less than about 25,000; 30,000; 35,000; 40,000; 45,000; or 50,000 psi. In some embodiments, a pressure of about 33,155 psi is used. In various embodiments, a cold isostatic press that is rated at approximately 66,000 psi can be used for the CIP procedure.

At stage 186, the multi-layer part is removed from the isopress mold. At stage 188, the multi-layer part is heat treated. For example, the multi-layer part can be sintered and hot isostatic pressed. In some instances, the multi-layer part is subjected to a ceramic firing process that includes a binder burn-out (or pre-sinter) firing run, a sintering run, and a hot isopressing run, which can densify and harden the multi-layer part.

Figure 10:
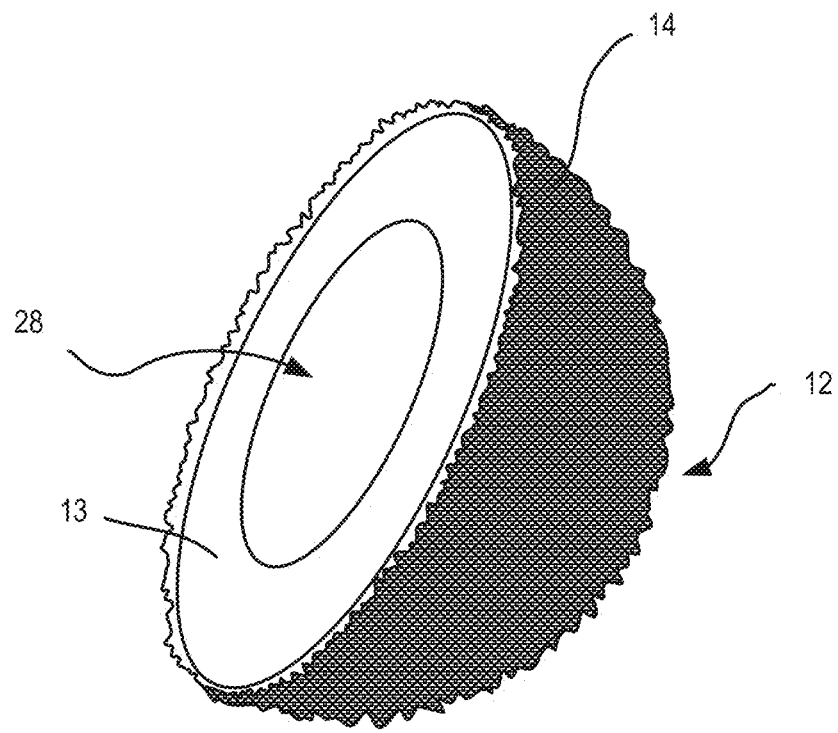
FIG. 10 is a perspective view of an embodiment of a multi-layer part that includes a base piece and an outer layer of coating particles that have been joined via the method of FIG. 9, wherein the multi-layer part is shown in a green state.

FIG. 10 is a perspective view of a multi-layer part—in particular, a monoblock cup 12—that has been formed by the methods 102, 104', and 180. The monoblock cup 12 is shown in a green state. The outer layer 14 and the inner cup 13 have been tightly joined into a monolithic piece via CIP at approximately 33,155 psi.

Figure 11:
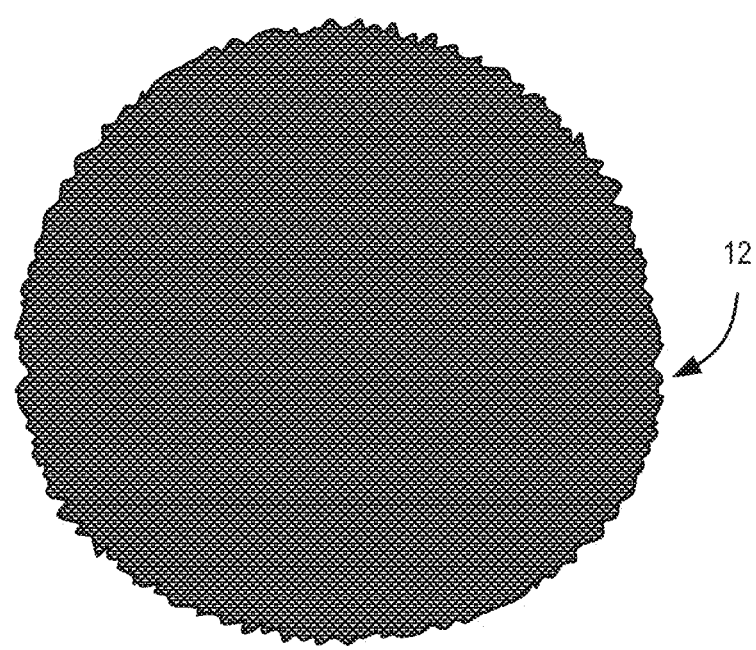
FIG. 11 is another perspective view of the multi-layer part of FIG. 10, shown after firing.

FIG. 11 is a perspective view of the monoblock cup 12 of FIG. 10 after sintering and hot isostatic pressing. The monoblock cup 12 may be slightly smaller after the firing process.

Figure 12A:
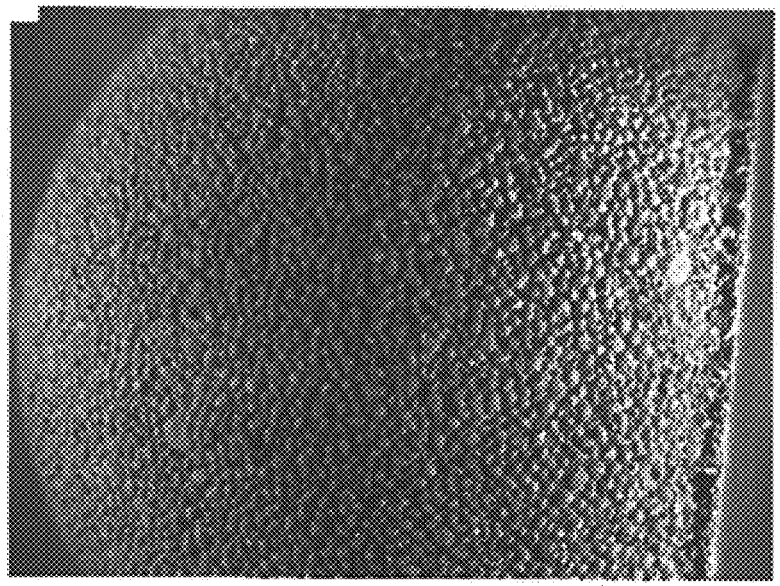
FIG. 12A is a stereomicroscope photograph of the outer layer of the multi-layer part of FIG. 11, wherein the scale depicted in the insert at the upper left-hand corner of the photograph defines a length of 1000 μm.
Figure 12B:
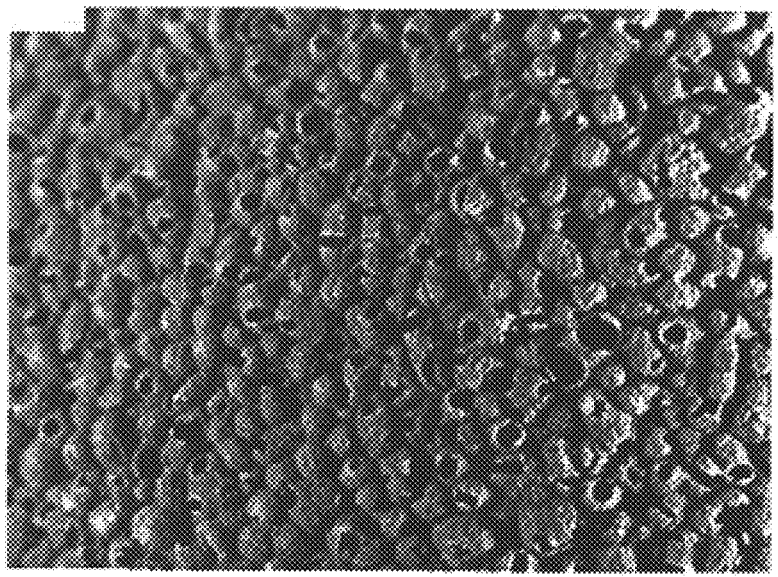
FIG. 12B is another stereomicroscope photograph of the outer layer of the multi-layer part of FIG. 11 showing greater detail, wherein the scale depicted in the insert at the upper left-hand corner of the photograph defines a length of 1000 μm.
Figure 12C:
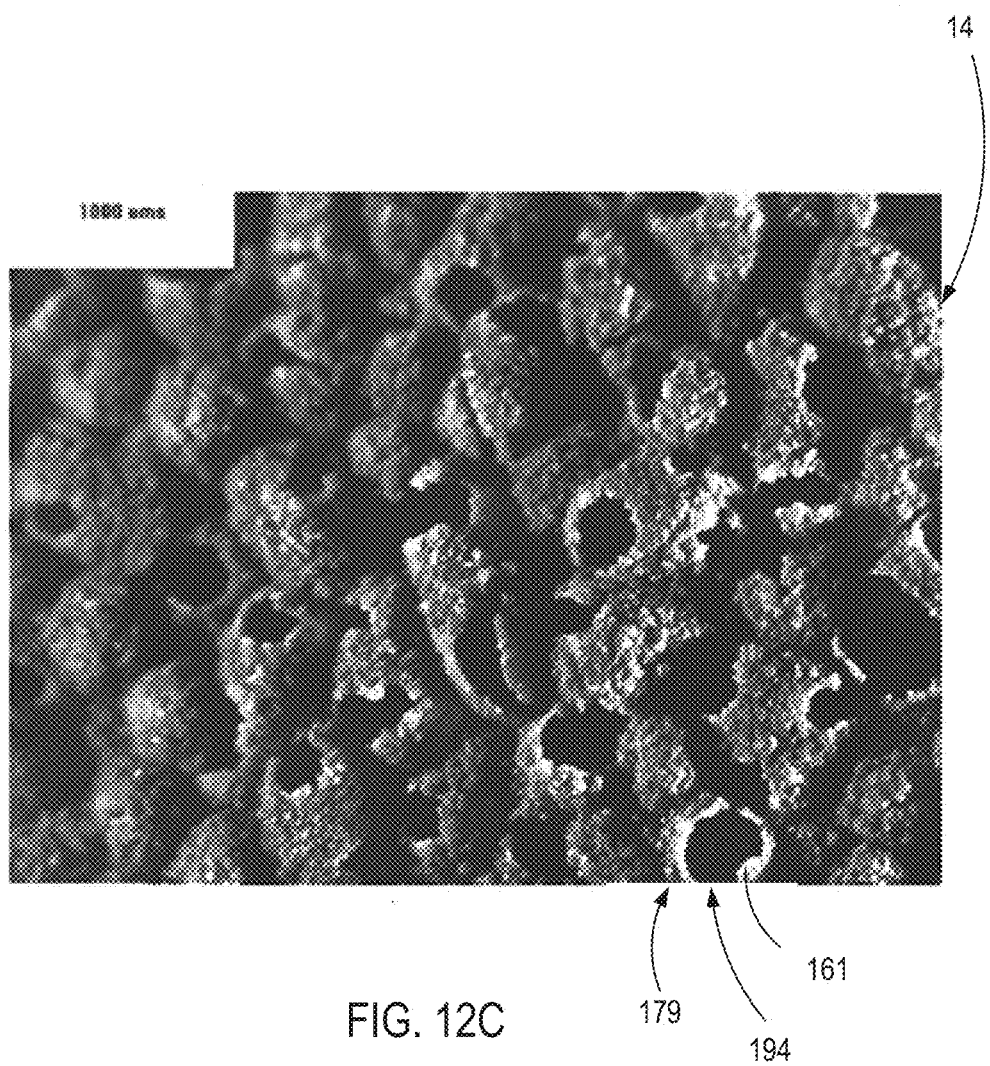
FIG. 12C is another stereomicroscope photograph of the outer layer of the multi-layer part of FIG. 11 showing even greater detail, wherein the scale depicted in the insert at the upper left-hand corner of the photograph defines a length of one millimeter.

FIGS. 12A-12C are different views of the outer layer 14. As can best be seen in FIG. 12C, the firing process can cause the pore former material to evaporate and leave behind large pores 194. For example, one coating particle 179 is identified in FIG. 12C. The coating particle 179 originally included a pore former core that was attached to and surrounded by a layer of ceramic powder 161. However, after firing, only the ceramic powder layer 161 remains, which has been compacted and sintered into a structure that is unified with the remainder of the monoblock cup 12.

The outer layer 14 is thus relatively porous (particularly as compared with the inner cup 13), and can be well-suited for attachment to bone. Stated otherwise, the textured layer 14 can have a high and controlled porosity that acts as a matrix to securely attach the monoblock cup 12 to natural patient bone.

Figure 13:
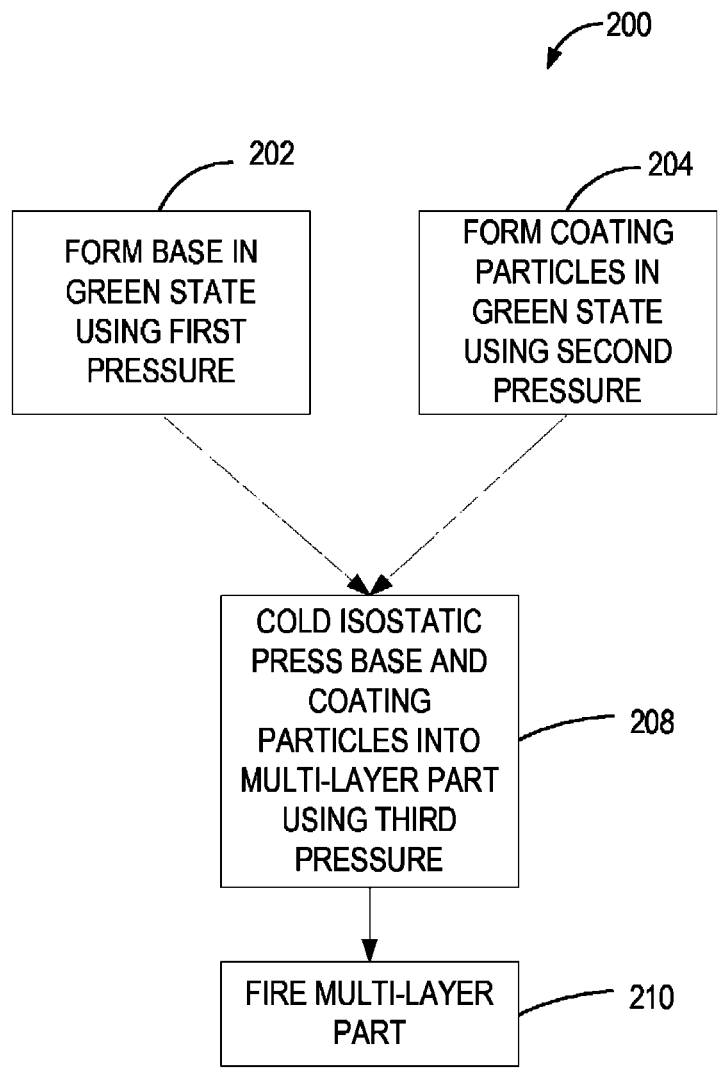
FIG. 13 is a flow chart that depicts another illustrative method for forming a multi-layer part, such as the acetabular cup of FIG. 1B, that has a variable density.

FIG. 13 depicts another illustrative method 200 for manufacturing a multi-layer ceramic part, such as the monoblock cup 12 discussed above. Method 200 can resemble method 100 in many respects. For example, in some instances, a process used to create a monoblock cup 12 can proceed via one or more of the stages described with respect to each of methods 100, 200 (e.g., there can be partial or complete overlap between methods 100, 200). Accordingly, although certain processes described hereafter are discussed in relation to method 200, it is noted that such processes may also be suitably employed with method 100.

At stage 202, a base is formed in a green state using a first pressure. For example, the stage 202 can comprise the method 102 described above, in which CIP is used to form a partially compacted base.

At stage 204, coating particles are formed in a green state using a second pressure. For example, the stage 204 can comprise any of methods 300, 400, 400', 500, 500' discussed below.

At stage 208, the base and coating particles are compacted together via CIP so as to form a multi-layer part. The CIP is conducted at a third pressure. In some embodiments, the third pressure is greater than the first pressure, such that the base portion that is formed at stage 202 is compacted even further at stage 208, which can assist in fusing the coating particles with the base and thus strengthen the base/coating interface (i.e., the region between the base 13 and the outer layer 14). In other or further embodiments, the second pressure is greater than the first pressure, such that the coating particles may be compacted by a lesser amount than the base during stage 208. In some embodiments, each of the first, second, and third pressures are different from each other, whereas in other embodiments, two or more of the pressures (e.g., the second and third pressures) may be about the same. For example, when the second pressure is about the same as the third pressure, the coating particles may primarily be compacted into the outer surface of the base 13, without themselves being compressed to a smaller size. When the third pressure is greater than the second pressure, additional compression of the coating particles may also be achieved during the stage 208.

In embodiments and implementations in which the second pressure is at least substantially the same as the third pressure, the compression of the particles may be limited in order to increase porosity, which may be useful for some purposes. In embodiments and implementations in which the third pressure is significantly higher than the second pressure, certain particles may be compacted to reduce porosity but provide increased bonding strength between the coating and the base, which may also be useful for some purposes.

At stage 210, the multi-layer part is fired in any suitable manner, such as those discussed above.

Figure 14:
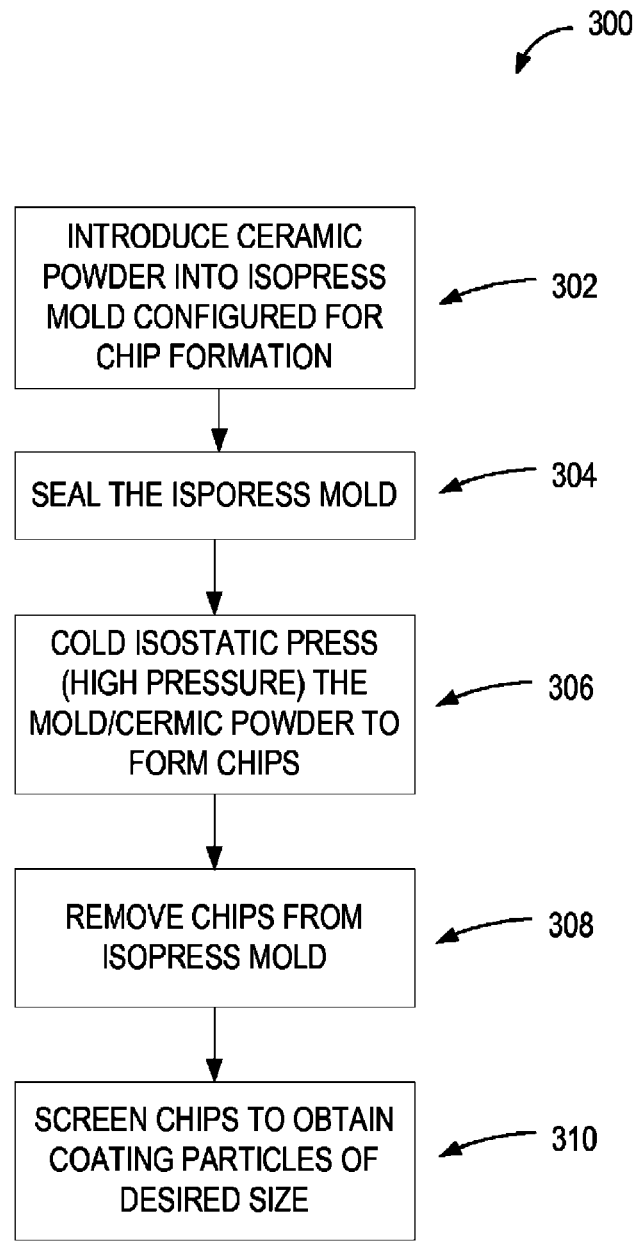
FIG. 14 is a flow chart that depicts an illustrative method of forming coating particles that can be mounted to a base piece, such as that shown in FIG. 5.

FIG. 14 depicts another method 300 for forming coating particles. At stage 302, ceramic powder is introduced into an isopress mold that is configured for compressing the powder into chips, as discussed further below. At stage 304, the isopress mold is sealed. At stage 306, the mold and ceramic powder are compressed via CIP, which forms chips from the ceramic powder. At stage 308, the chips are removed from the isopress mold. At stage 310, the chips are screened to obtain coating particles of a desired size.

Figure 15A:
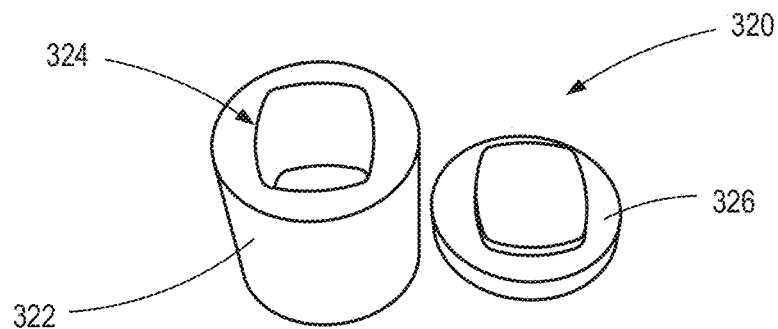
FIG. 15A is a perspective view of an embodiment of an isopress mold.
Figure 15B:
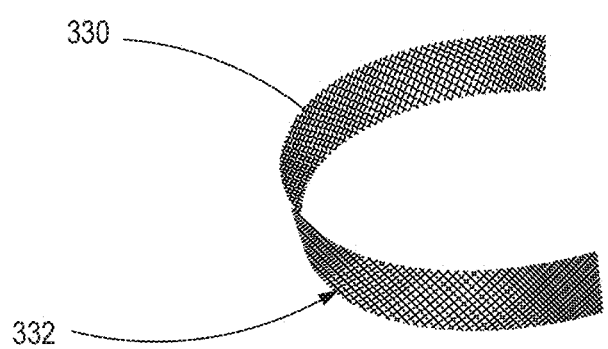
FIG. 15B is a perspective view of an embodiment of a screen configured for use with the isopress mold of FIG. 15A.
Figure 15C:
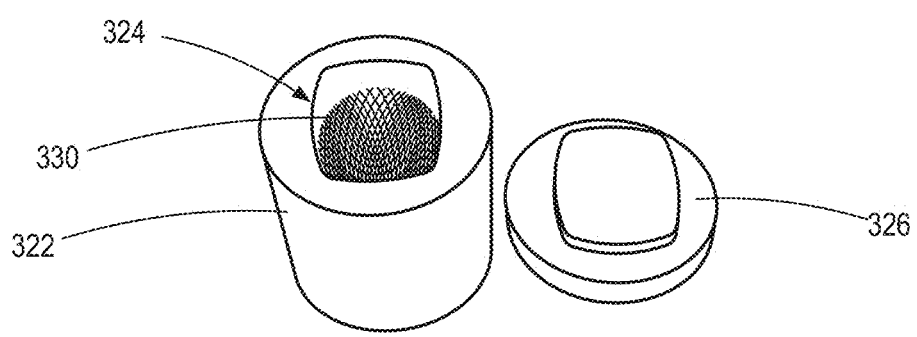
FIG. 15C is a perspective view of the screen of FIG. 15B rolled up and inserted in the isopress mold of FIG. 15A.

FIGS. 15A-15C illustrate CIP tooling that can be used to form chips in accordance with the method 300. The tooling includes an isopress mold 320 that includes a base portion 322 and a lid 326. The base portion 322 defines a cavity 324 into which a screen mesh 330 can be received. The screen mesh 330 can comprise any suitable material that is capable of maintaining its conformation under high pressures, yet is capable of being oriented (e.g., rolled) into an orientation in which it can be inserted into the cavity 324 (FIG. 15C). In some embodiments, the screen mesh 330 comprises plastic.

The screen mesh 330 can define a series of regularly or irregularly sized and spaced openings 332 of any desired size and shape. In the illustrated embodiment, the openings are shaped as diamonds. Other shapes can include, for example, circles, squares, ovals, etc. The openings 332 can be of any suitable or desired size. In various embodiments, a maximum diameter of the openings 332 is within a range of from about 0.5 to about 5.0 millimeters, from about 1.0 to about 4.0 millimeters, or from about 1.5 to about 3.5 millimeters, is no greater than about 1.0, 1.5, 2.0, 2.5, 3.0, 3.5, 4.0, 4.5, or 5.0 millimeters, or is no less than about 1.0, 1.5, 2.0, 2.5, 3.0, 3.5, 4.0, 4.5, or 5.0 millimeters, depending on the desired properties of the chips formed thereby.

With reference to FIG. 15C, after the screen mesh 330 and ceramic powder have been introduced into the base portion 322, the lid 326 can be secured to the base portion 322 and may be sealed in place in any suitable manner, such as via silicone tape.

CIP can then be performed on the mold/powder, and the coiled screen mesh 330 can cause the powder to be compacted into chips. The CIP can be performed in any suitable cold isostatic press, such as one that is rated up to 66,000 psi. In various embodiments, pressures used for the CIP at stage 184 are within a range of from about 20,000 psi to about 60,000 psi; from about 25,000 psi to about 50,000 psi, or from about 30,000 psi to about 40,000 psi; the pressures are no greater than about 25,000; 30,000; 35,000; 40,000; 45,000; or 50,000 psi; or the pressures are no less than about 25,000; 30,000; 35,000; 40,000; 45,000; or 50,000 psi. In some embodiments, a pressure of about 33,155 psi is used.

Figure 16A:
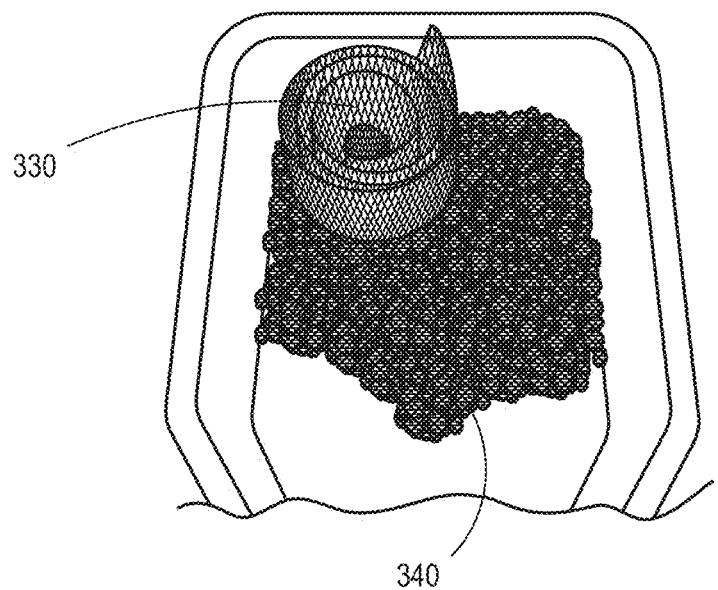
FIG. 16A is a perspective view of the screen of FIG. 15B and coating particles that have been formed thereby, which have been removed from the isopress mold of FIG. 15A, wherein the screen remains in a rolled configuration.
Figure 16B:
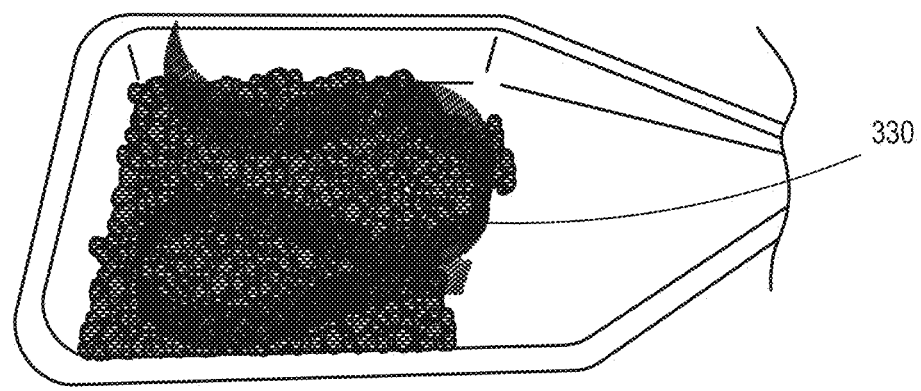
FIG. 16B is another perspective view of the screen of FIG. 15B and coating particles that have been formed thereby, which have been removed from the isopress mold of FIG. 15A, wherein the screen has been extended from the rolled configuration.

As shown in FIG. 16A, after the CIP procedure, the isopress mold 320 can be opened and the newly formed ceramic chips 340 and the screen mesh 330 can be removed. As shown in FIG. 16B, the screen mesh 330 may be unwound to assist in removal of the chips 340.

The chips can be screened in any suitable manner to obtain chips of the desired shape and/or size. In some instances, a Ro-Tap® stackable test sieve shaker available from W.S. Tyler of Mentor, Ohio may be used. Sieve sizes that may be used may have openings sized at 250, 425, 500, 710, 1000, 1700, and/or 2800 microns. Other sieve sizes are also possible, depending on the application. In various embodiments, chips that are used in forming a monoblock cup may be in the range of from about 100 microns to about 4000 microns, from about 100 microns to about 3500 microns, from about 500 microns to about 2500 microns, from about 250 microns to about 710 microns, from about 710 microns to about 1700 microns, from about 1000 to about 2800 microns, from about 250 to about 2800 microns, from about 250 to about 1700 microns, or from about 1700 microns to about 2800 microns. Other sub-ranges within the foregoing ranges, as well as other ranges, are also possible.

After screening of the ceramic chips 340 into the desired size, sizes, or size range, the desired chips may then be introduced into an isopress mold with a partially compacted inner cup or base 13. Accordingly, the ceramic chips 340, which may also be referred to as coating particles, may be combined with the base 13 in any suitable manner, such as in accordance with the method 180 discussed above with respect to FIG. 9.

Figure 17A:
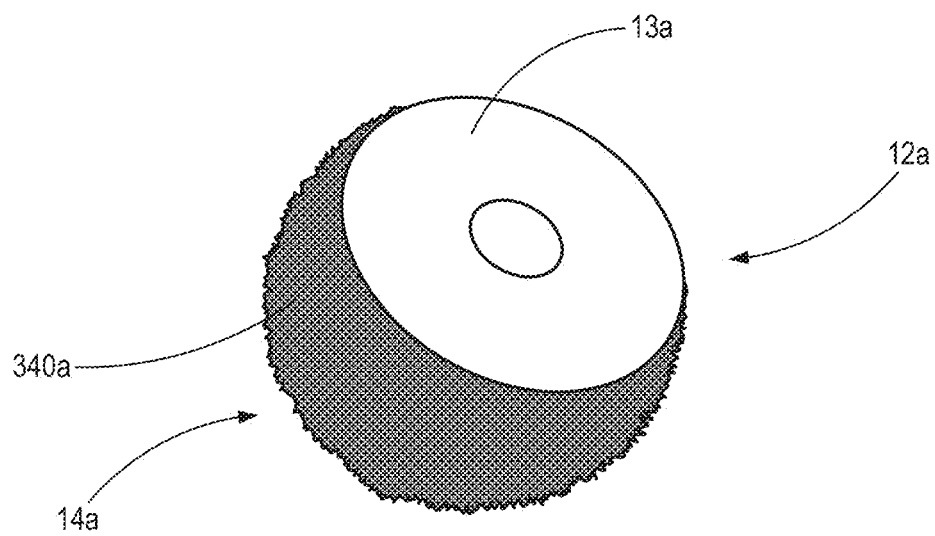
FIG. 17A-17C are perspective views of three different embodiments of multi-layer ceramic parts that have been formed in accordance with the methods of FIGS. 13 and 14, wherein the coating particles that form an outer layer of the ceramic part are progressively larger, and wherein the multi-layer parts are shown in a green state.
Figure 17B:
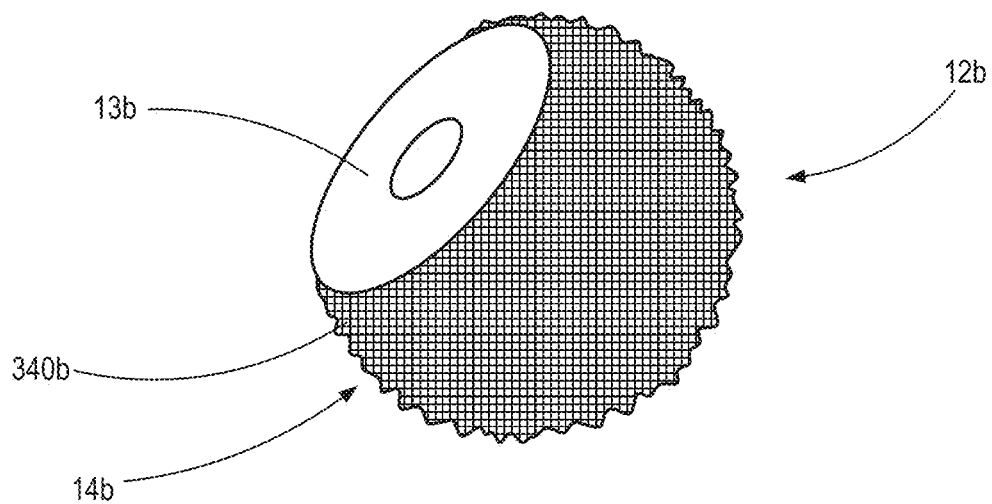
Figure 17C:
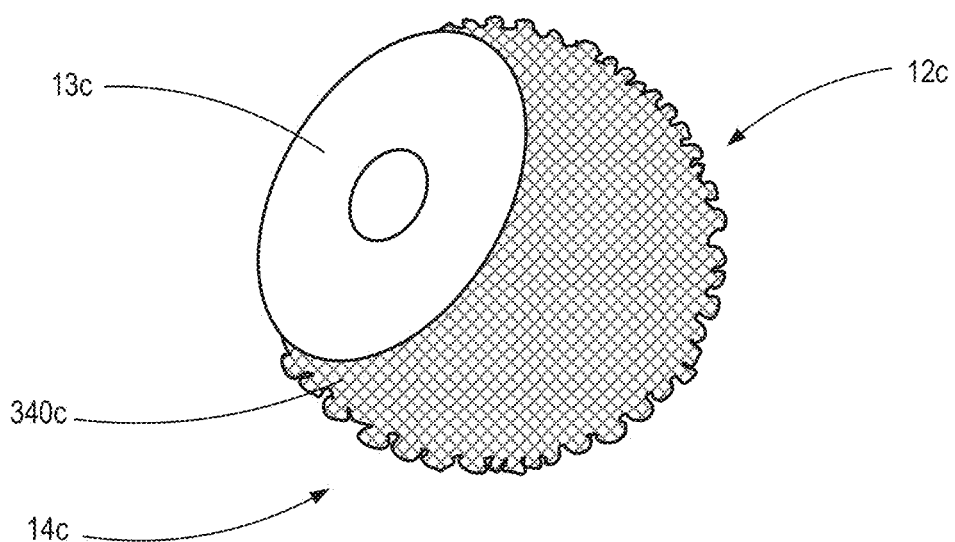

Each of FIGS. 17A-17C depicts a different implant in a green state that was formed in accordance with methods 200, 102, 300, and 180 of FIGS. 13, 3, 14, and 9, respectively. In FIG. 17A, an implant part 12a includes chips 340a having sizes ranging from about 250 to about 710 microns; in FIG. 17B, an implant part 12b includes chips 340b having sizes ranging from about 710 to about 1700 microns; and in FIG. 17C, an implant part 12c includes chips 340c having sizes ranging from about 1000 to about 1800 microns. It should be understood that, although the implants shown in FIGS. 17A-17C appear to comprise femoral heads, it is unlikely that femoral head implants will be constructed with the most porous layers on the outside as depicted in these figures. These images are therefore for illustration purposes only. However, it should also be understood that manufacturing of a variety of different implants and other devices are contemplated within the context of this disclosure. These comments should therefore not be construed as limiting the scope of the invention in any way, shape, or manner.

Figure 18:
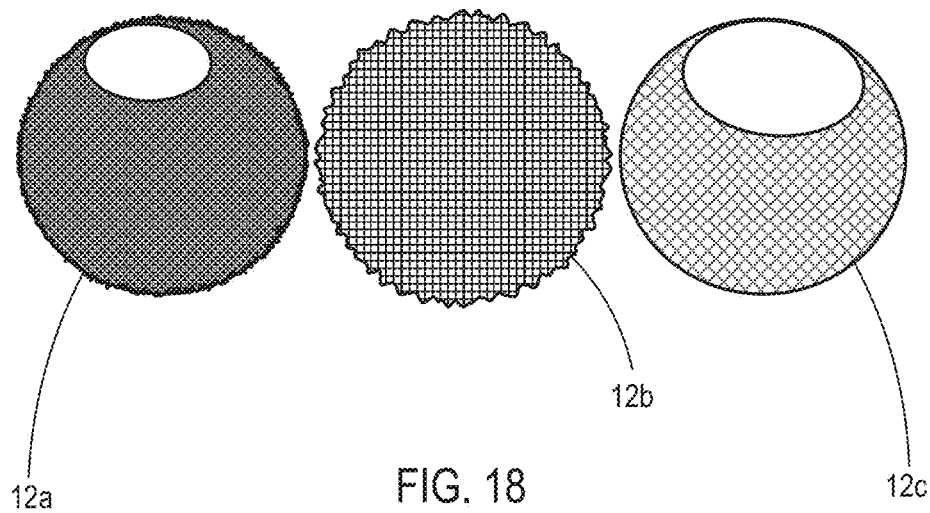
FIG. 18 is a perspective view of the multi-layer ceramic parts of FIGS. 17A-17C shown after firing, wherein the multi-layer parts on the left and right have been surface ground by different amounts.

FIG. 18 shows the implant parts 12a, 12b, and 12c after the cups have been fired. The cups 12a and 12c have been surface ground by different amounts.

Figure 19A:
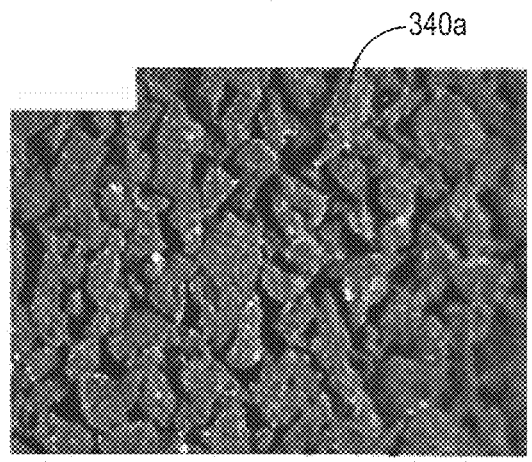
FIG. 19A is a stereomicroscope photograph of the outer layer of the multi-layer part of FIG. 17A, wherein the scale depicted in the insert at the upper left-hand corner of the photograph defines a length of 1000 μm.
Figure 19B:
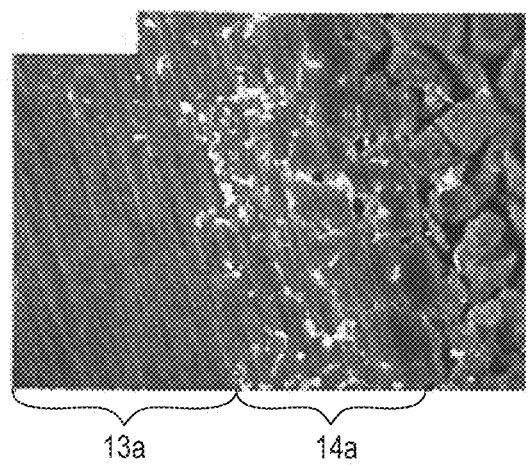
FIG. 19B is a stereomicroscope photograph of a cross-section of the multi-layer part of FIG. 17A, wherein the scale depicted in the insert at the upper left-hand corner of the photograph defines a length of 1000 μm.
Figure 19C:
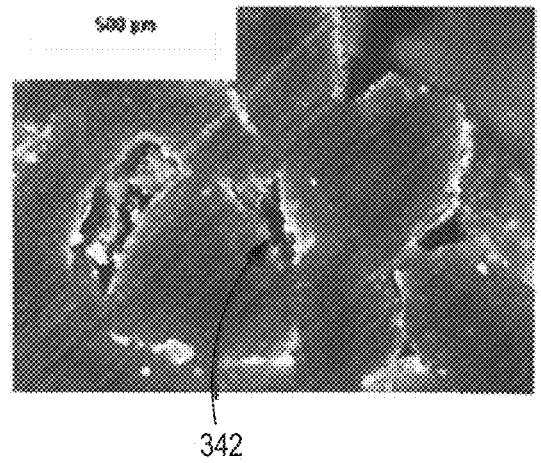
FIG. 19C is a stereomicroscope photograph of a cross-section of the multi-layer part of FIG. 17A, wherein the scale depicted in the insert at the upper left-hand corner of the photograph defines a length of 500 μm.
Figure 20A:
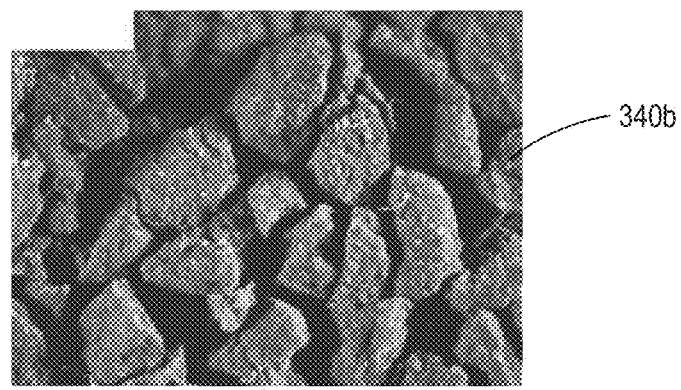
FIG. 20A is a stereomicroscope photograph of the outer layer of the multi-layer part of FIG. 17B, wherein the scale depicted in the insert at the upper left-hand corner of the photograph defines a length of 1000 μm.
Figure 20B:
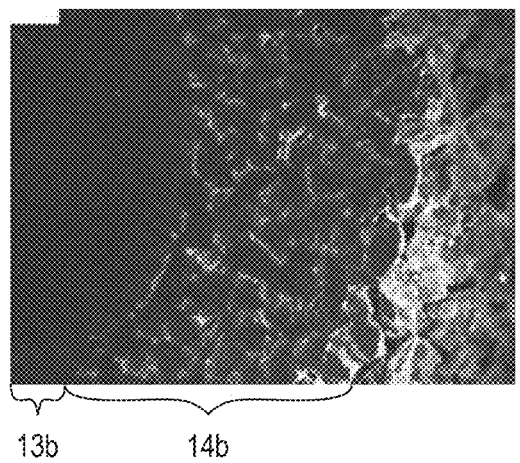
FIG. 20B is a stereomicroscope photograph of a cross-section of the multi-layer part of FIG. 17B, wherein the scale depicted in the insert at the upper left-hand corner of the photograph defines a length of 1000 μm.
Figure 20C:
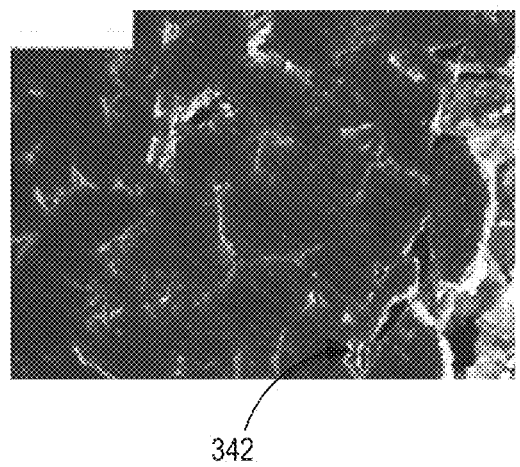
FIG. 20C is a stereomicroscope photograph of a cross-section of the mutli-layer part of FIG. 17B, wherein the scale depicted in the insert at the upper left-hand corner of the photograph defines a length of 1000 μm.
Figure 21A:
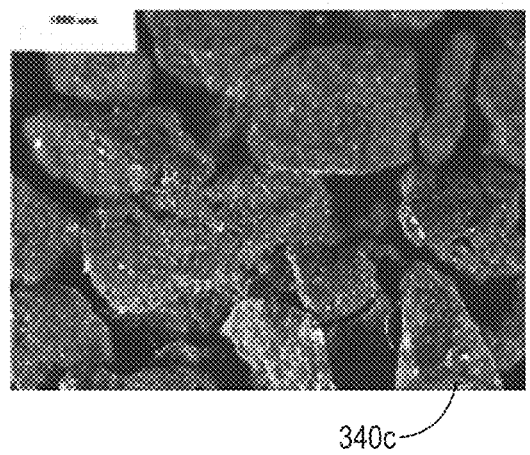
FIG. 21A is a stereomicroscope photograph of the outer layer of the multi-layer part of FIG. 17C, wherein the scale depicted in the insert at the upper left-hand corner of the photograph defines a length of 1000 μm.
Figure 21B:
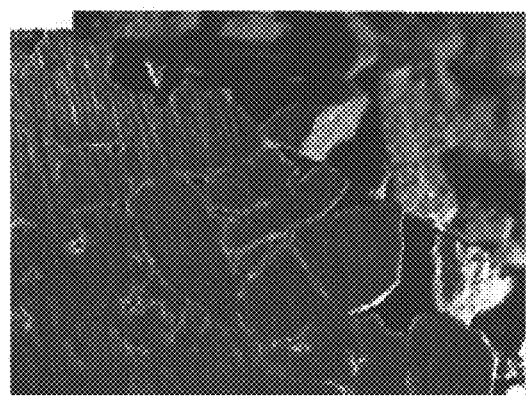
FIG. 21B is a stereomicroscope photograph of a cross-section of the multi-layer part of FIG. 17C, wherein the scale depicted in the insert at the upper left-hand corner of the photograph defines a length of 1000 µm.
Figure 21C:
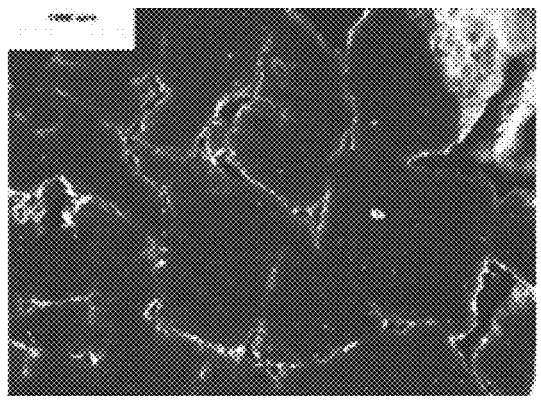
FIG. 21C is a stereomicroscope photograph of a cross-section of the mutli-layer part of FIG. 17C, wherein the scale depicted in the insert at the upper left-hand corner of the photograph defines a length of 1000 µm.

FIG. 19A shows a surface view of the monoblock cup 12a, and FIGS. 19B and 19C show cross-sectional views of the monoblock cup 12a at different magnifications. In various embodiments, a thickness of the outer layer 14a, as seen in FIG. 19B, can be within a range of from about 1.0 to about 5.0 millimeters or from about 1.5 to about 2.5 millimeters, or can be no less than about 1.0, 2.0, 3.0, 4.0. or 5.0 millimeters. The interface between the outer layer 14a and the inner cup 13a can be extremely strong. For example, in some embodiments, the interface has a strength of greater than about 30 megapascals, as determined by a tensile strength test. Such a tensile test may be similar or identical to the ASTM C633 Standard Test Method for Adhesion or Cohesion Strength of Thermal Spray Coatings, for example.

As shown in FIG. 19C, the outer layer 14a can include a number of pores 342, which are positioned between adjacent coating particles (i.e., chips, in the present embodiment). The porosity of the outer layer 14a can be readily controlled by the size of the coating particles and the types of coating particles used, as further discussed below.

FIGS. 20A-20C and 21A-21C show similar features for the monoblock cups 12b and 12c. In general, the outer layers 14a, 14b, 14c can provide aggressive textures with porosity that acts as a matrix to secure the monoblock cups to natural patient bone. Additionally, the layers 14a, 14b, 14c can be fused very strongly to the inner cups 13a, 13b, 13c.

Figure 22:
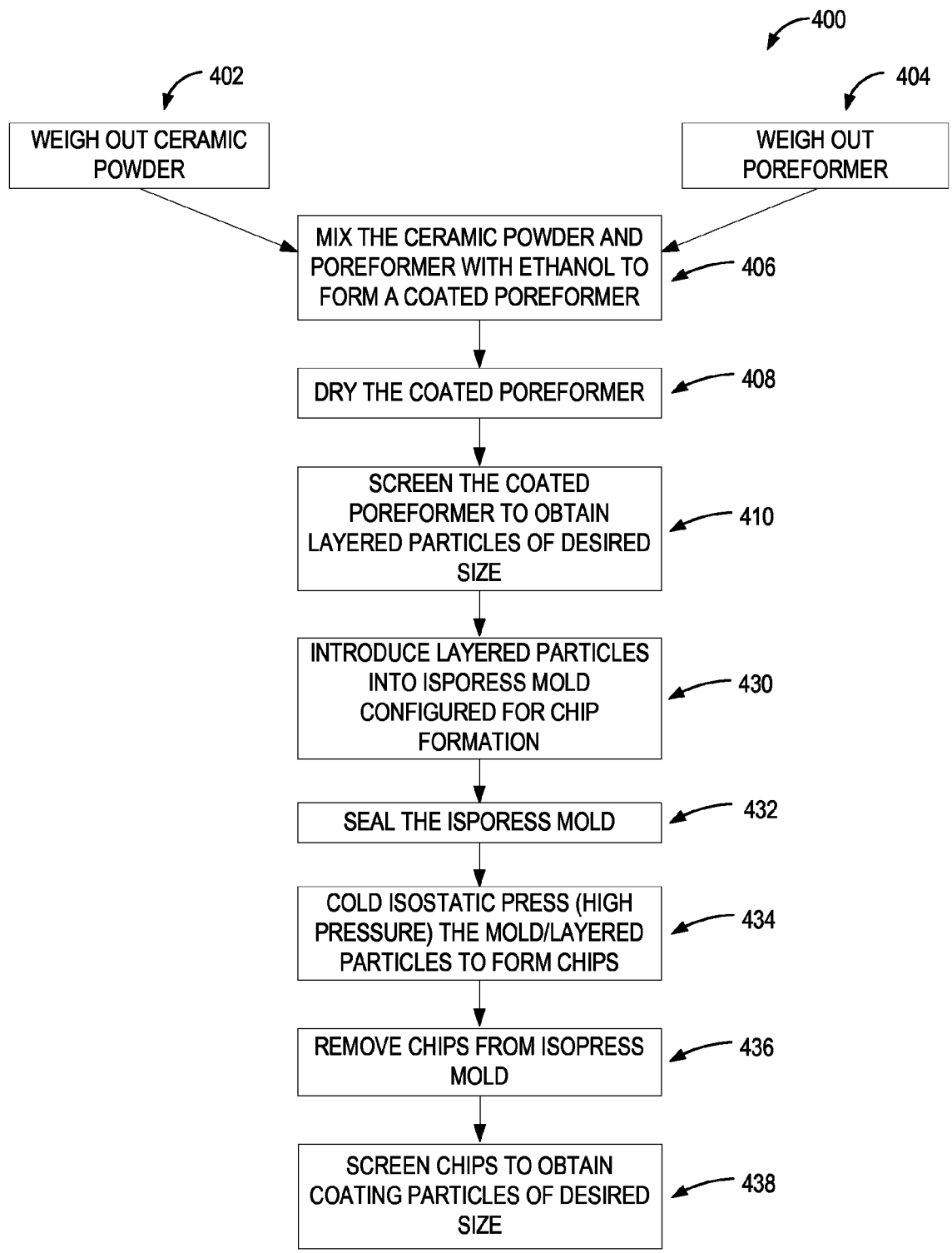
FIG. 22 is a flow chart that depicts another illustrative method of forming coating particles that can be mounted to a base piece, such as that shown in FIG. 5.

FIG. 22 depicts another method 400 for forming coating particles. The method 400 is a hybrid of the methods 104 and 300 discussed above. Stages 402, 404, 406, and 408 may be identical to the stages 160, 162, 164, and 170, respectively, of the method 104, which is described above with respect to FIG. 7, and thus will not be repeated here. These stages of the method 400 yield layered particles that have pore former cores and ceramic powder coatings. At stage 410, the coated pore formers are screened to obtain such layered particles of the desired size. An example of such layered particles 450, having pore former cores 452 and ceramic powder coatings 454, is shown in FIG. 24.

Figure 26:
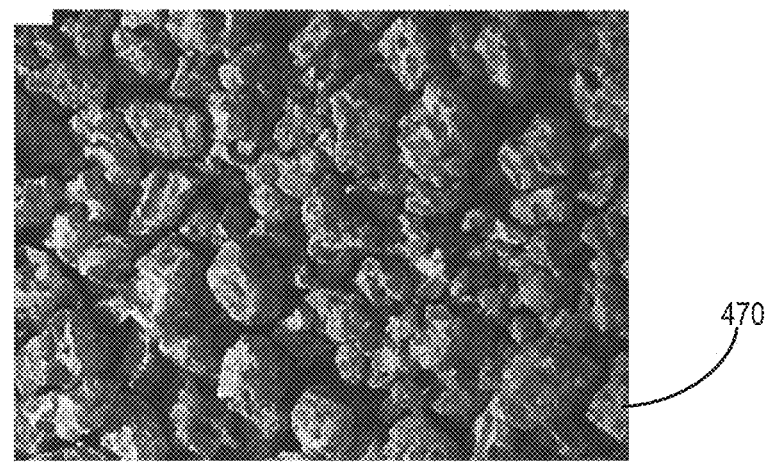
FIG. 26 is an enlarged perspective view of the coating particles of FIG. 25, wherein the scale depicted in the insert at the upper left-hand corner of the photograph defines a length of 1000 µm.

With continued reference to FIG. 22, stages 430, 432, 434, 436, and 438 may be identical to the stages 302, 304, 306, 308, and 310, respectively, of the method 300, which is described above with respect to FIG. 14, with the exception that the layered particles obtained in stage 410 are used in place of the ceramic powder of the method 300. Accordingly, the chips, or coating particles, obtained via the method 400 are in fact chips that include pore former cores and ceramic powder coatings. An example of these coating particles is shown in FIG. 26.

Figure 23:
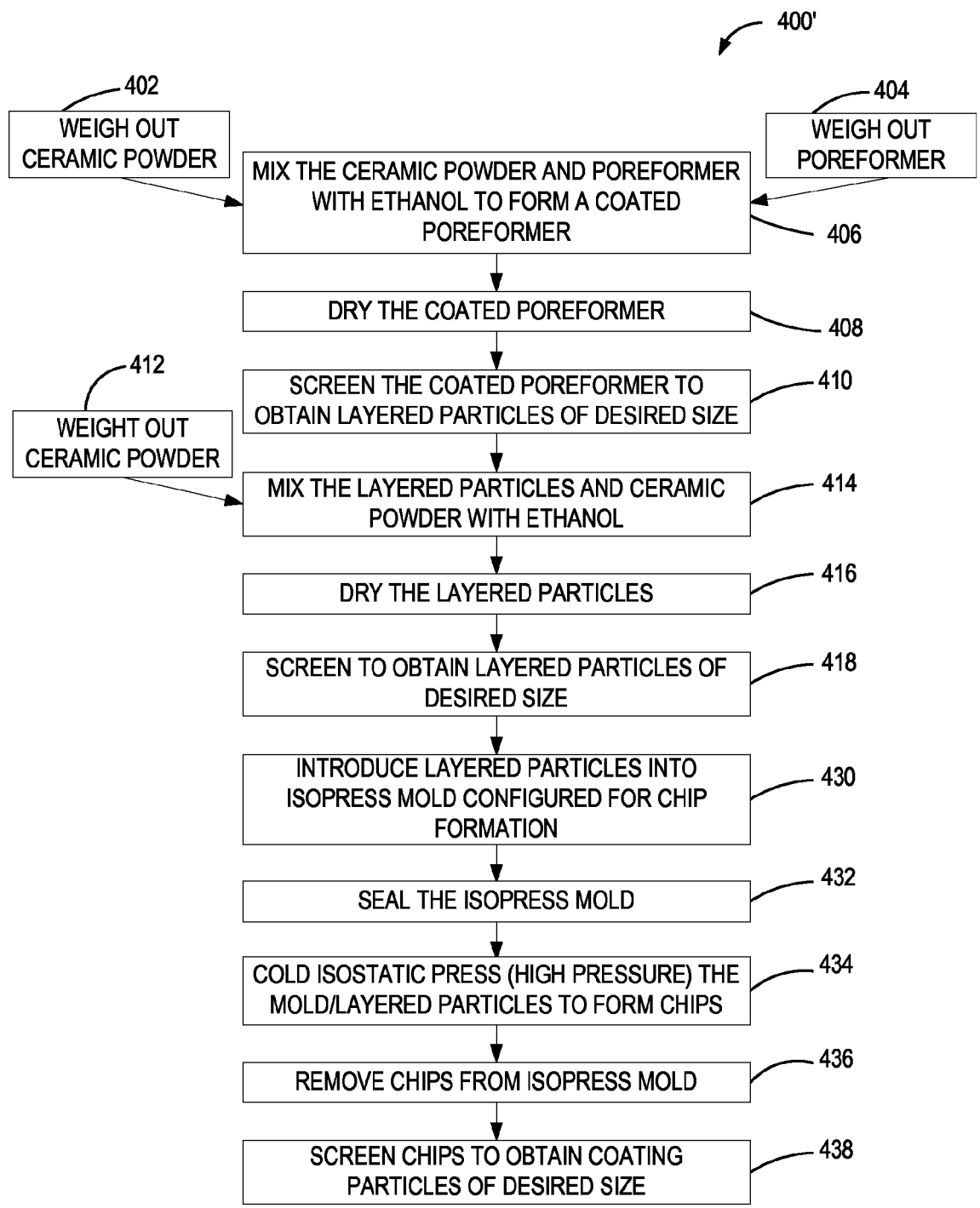
FIG. 23 is a flow chart that depicts another illustrative method of forming coating particles that can be mounted to a base piece, such as that shown in FIG. 5.

FIG. 23 depicts another method 400' for forming coating particles. The method 400' is a hybrid of the methods 104' and 300 discussed above. Accordingly, the primary difference between the methods 400 and 400' is that additional coating of the pore former cores with ceramic powder is performed at the additional stages 412, 414, 416, and 418.

Figure 24:
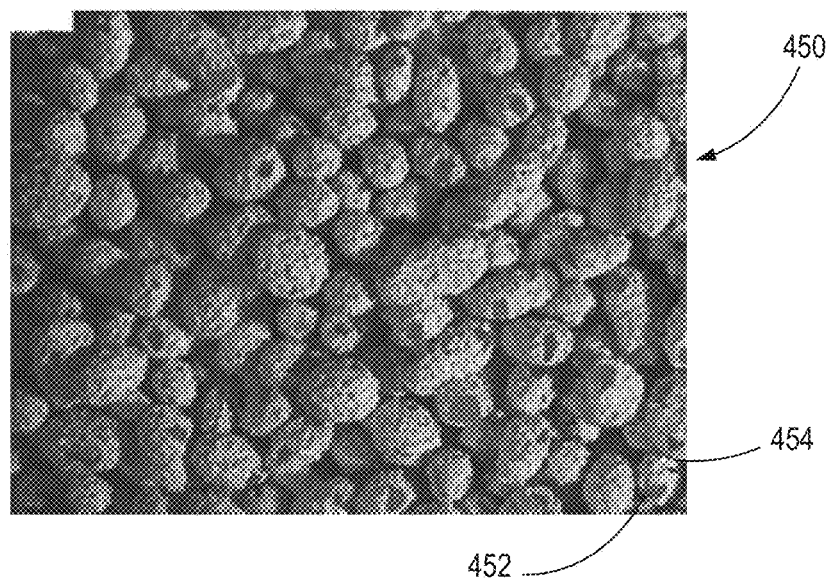
FIG. 24 is a perspective view of an embodiment of layered particles that are in a green state and have been formed in accordance with the method of FIG. 23, wherein the scale depicted in the insert at the upper left-hand corner of the photograph defines a length of 1000 µm.
Figure 25:
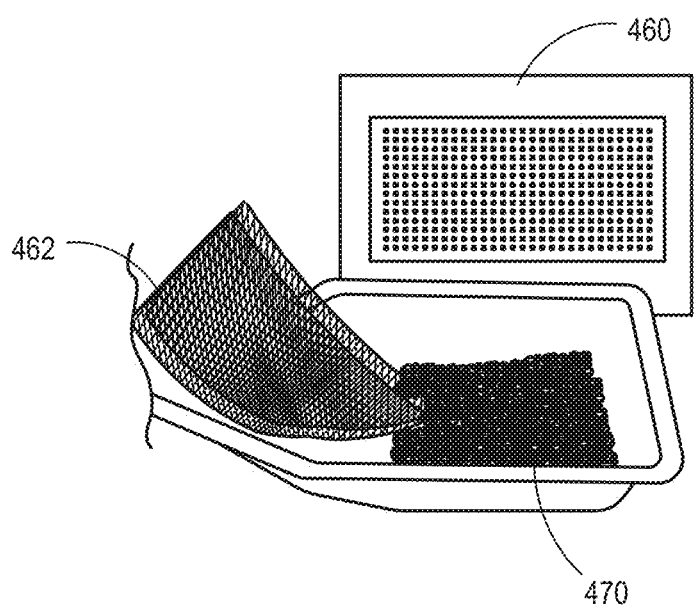
FIG. 25 is a perspective view of an embodiment of an isopress mold and an embodiment of a screen that have been used to convert the layered particles of FIG. 24 into coating particles, which are also shown.

As previously mentioned, FIG. 24 depicts an embodiment of layered particles 450 that have pore former cores 452 and ceramic powder coatings 454. With reference to FIG. 25, such layered particles 450 can be introduced into an isopress mold 460 with one or more mesh screens 462 in a manner such as that described above with respect to the tooling in FIGS. 15A-15C. However, in the embodiment illustrated in FIG. 25, a cavity defined by the isopress mold 460 is more planar, and multiple layers of mesh screens 462 are used, rather than coiling a single mesh screen. After introduction of the layered particles 450 and mesh screens 462 into the isopress mold 460, the isopress mold 460 may be sealed in any suitable manner. For example, in some embodiments, the isopress mold 460 may be vacuum sealed.

FIG. 25 also illustrates the chips or coating particles 470 that can be gathered after performing CIP on the mold 460 and layered particles 450. Stated otherwise, the layered particles 450 are converted into the coating particles 470. A close-up view of the coating particles 470 is provided in FIG. 26.

Screening of the coating particles 470 can proceed in any suitable manner, and can be used to isolate coating particles 470 of any desired size, or within a desired size range. In some instances, a Ro-Tap® stackable test sieve shaker available from W.S. Tyler of Mentor, Ohio may be used, as previously discussed. In some embodiments, coating particles 470 within a size range of 250 to 2800 microns may be used. Other size ranges are also contemplated.

After screening of the coating particles 470, the coating particles may then be introduced into an isopress mold with a partially compacted inner cup or base 13. Accordingly, the coating particles 470 may be combined with the base 13 in any suitable manner, such as in accordance with the method 180 discussed above with respect to FIG. 9.

Figure 27:
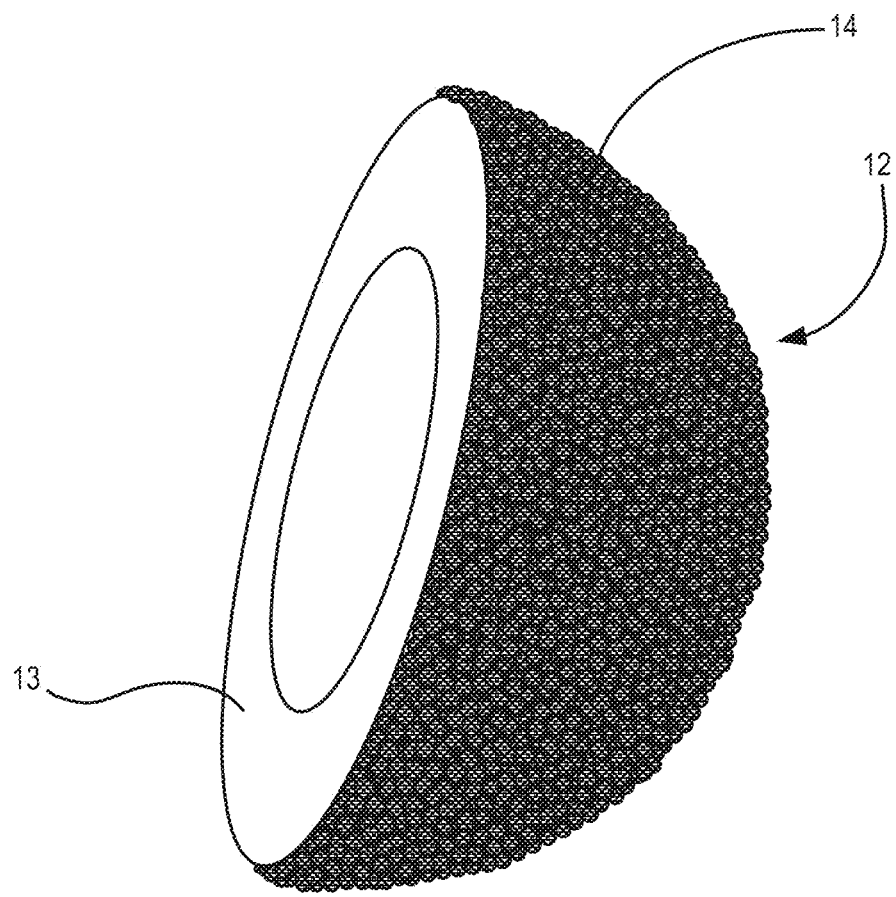
FIG. 27 is a perspective view of an embodiment of a multi-layer ceramic part that has been formed in accordance with the methods of FIGS. 13 and 23, and which is shown in a green state.
Figure 28A:
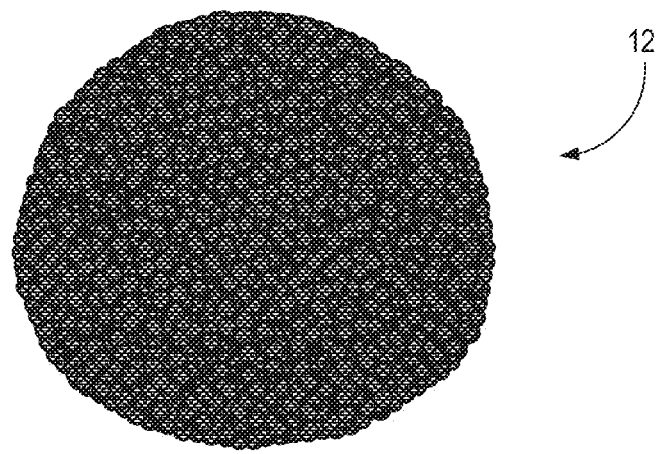
FIGS. 28A-28D are various perspective views and stereomicroscope photographs of the multi-layer ceramic part of FIG. 27 shown after firing, wherein the scale depicted in the insert at the upper left-hand corner of the photograph in FIG. 28D defines a length of 1000 µm.
Figure 28B:
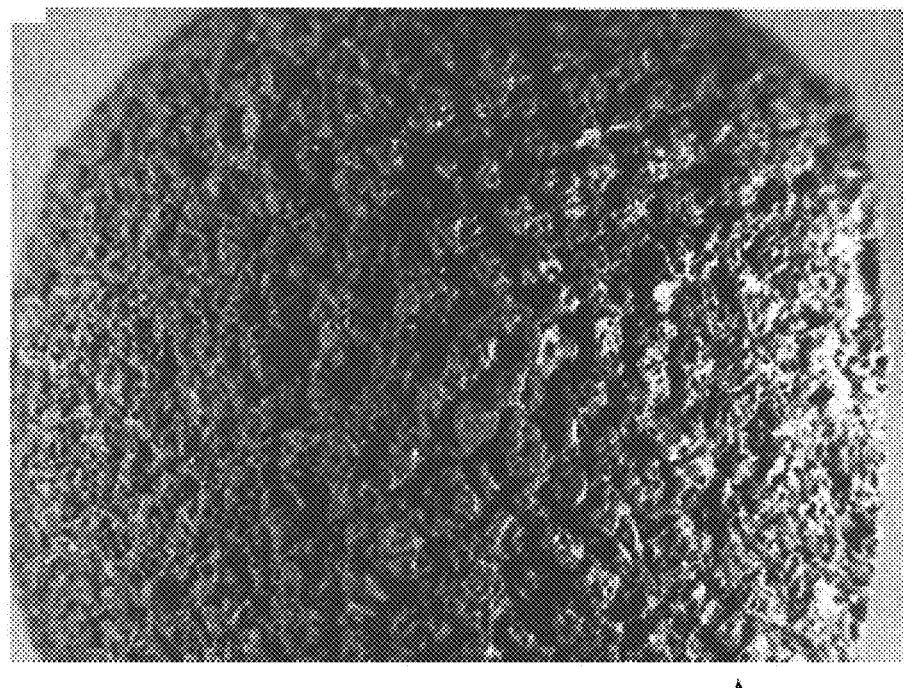
Figure 28C:
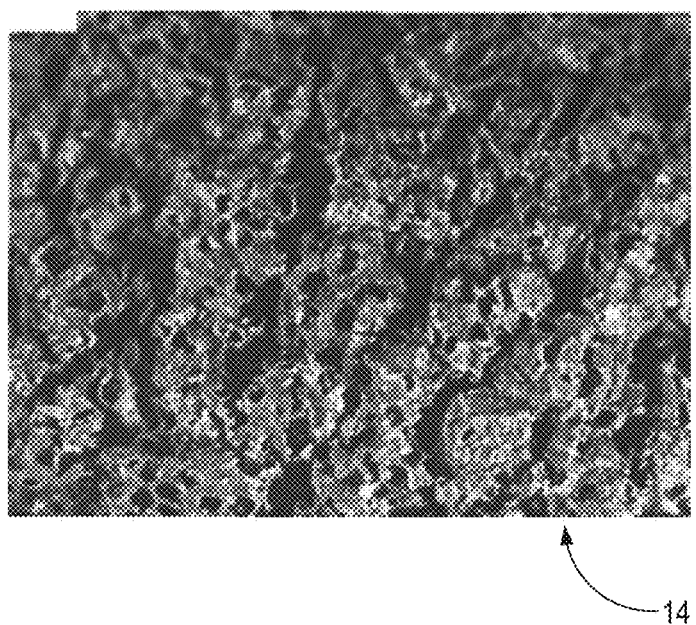
Figure 28D:
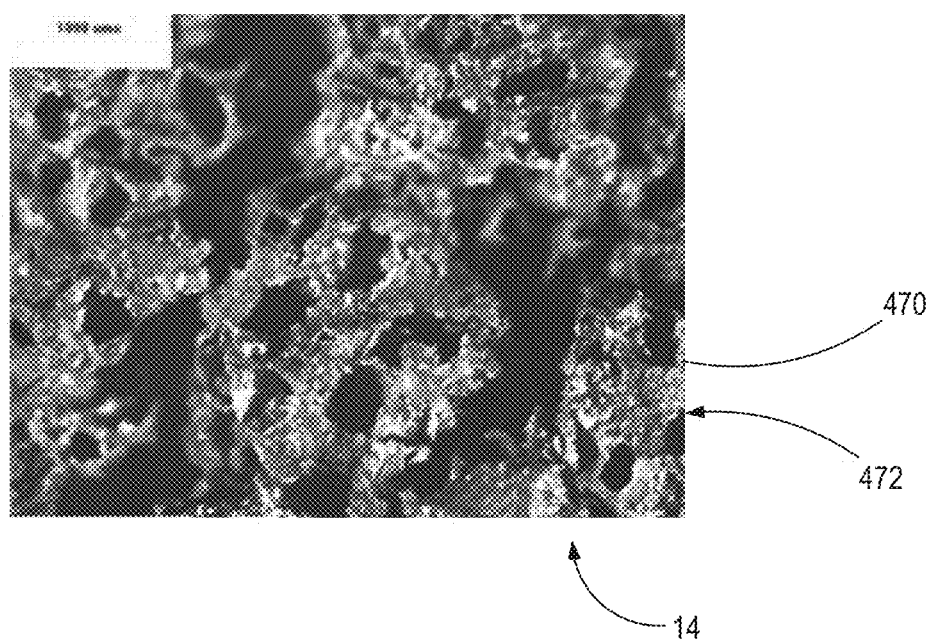

FIG. 27 depicts a monoblock cup 12 in a green state that was formed in accordance with methods 200, 102, 400', and 180 of FIGS. 13, 3, 23, and 9, respectively. FIGS. 28A-28D show the monoblock cup 12 after it has been fired and the pore former material has been expelled therefrom. As shown in FIG. 28D, the pore former material leaves behind pores 472, such that the outer layer 14 can have a texture with a high and controlled porosity that acts as a matrix to secure the monoblock cup 12 to natural patient bone.

In one illustrative example, the coating particles 470 are formed according to the following procedure. The details provided with respect to this procedure are not intended to limit the present disclosure generally, although inventive concepts and independently claimable subject matter may be present within such details. Approximately 22.4 grams of $Si_3N_4$ are weighed out, and approximately 5.6 grams of a wax pore former are weighed out. Both components are introduced into a plastic bottle. Approximately 7.6 grams of ethanol are introduced into the bottle and the bottle is then closed. The bottle is shaken (e.g., by hand or otherwise) for approximately 1 minute. The mixed contents are then poured into a weigh boat and permitted to dry (e.g., overnight). The approximately 28-gram mixture is screened via a 425 micron sieve. The screening rids the coated pore former of excess $Si_3N_4$ powder that did not adhere to the pore former. The screened pore former/$Si_3N_4$ combination is then combined with another 18 grams of $Si_3N_4$ powder in a plastic bottle. Approximately 7.6 grams of ethanol are introduced into the bottle and the bottle is then closed. The bottle is shaken (e.g., by hand or otherwise) for approximately 1 minute. The mixed contents are then poured into a weigh boat and are permitted to dry (e.g., overnight). The contents are then screened via a 425 micron sieve.

Cut layers of plastic screen mesh are placed inside of a silicone isopress mold. The powder-coated pore former is then inserted into the isopress mold. The isopress mold is then sealed via a Seal-a-Meal® vacuum storage bag using a Seal-a-Meal® vacuum sealer available from Sunbeam Products, Inc. The isopress mold is then placed in a 66,000 cold isostatic press and isopressed at 33,155 psi.

The coating particles, or chips, that may be obtained via the methods 300, 400, and 400' discussed above may be substantially asymmetrical. In other methods, such as discussed hereafter, the coating particles may have one or more symmetries. For example, in some embodiments, spherical beads may be formed that exhibit multiple symmetries. Any desired shape or configuration for the coating particles may be formed, and such predictability or regularity may be more readily achieved via certain processes discussed hereafter.

Figure 29:
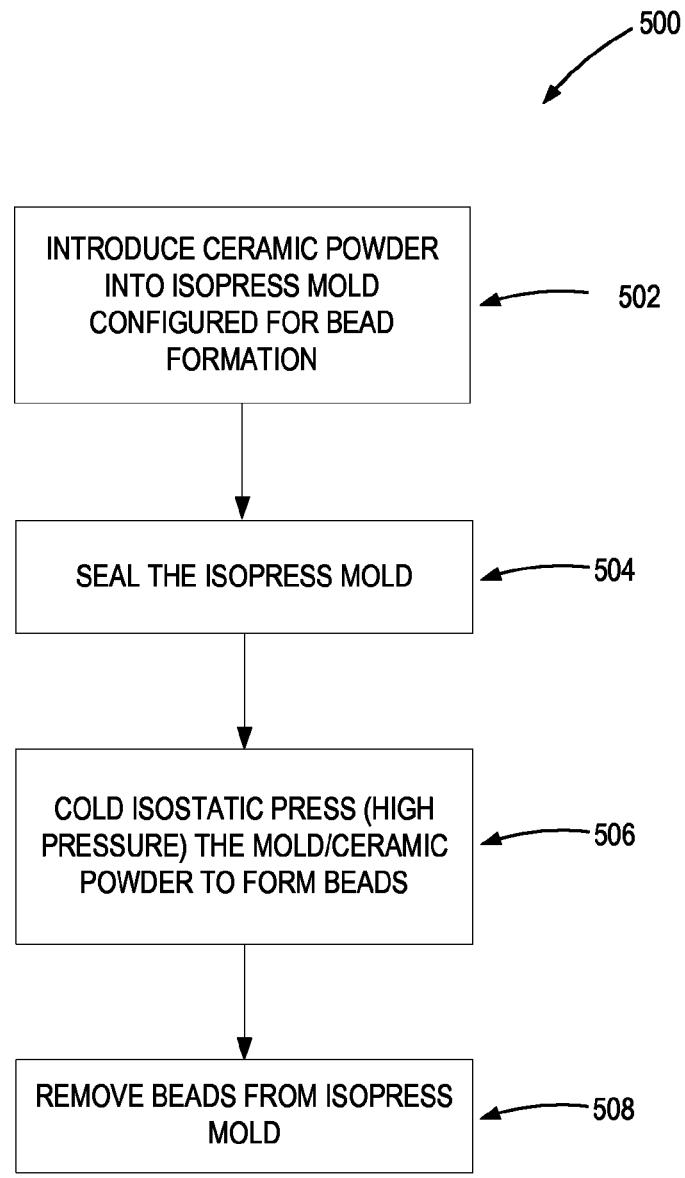
FIG. 29 is a flow chart that depicts another illustrative method of forming coating particles that can be mounted to a base piece, such as that shown in FIG. 5.

FIG. 29 depicts another method 500 for forming coating particles. At stage 502, ceramic powder is introduced into an isopress mold that is configured to form particles or beads of a desired configuration, as discussed further below. At stage 504, the isopress mold is sealed. At stage 506, the mold and ceramic powder are compressed via CIP, which forms beads from the ceramic powder. At stage 508, the beads are removed from the isopress mold.

Figure 30:
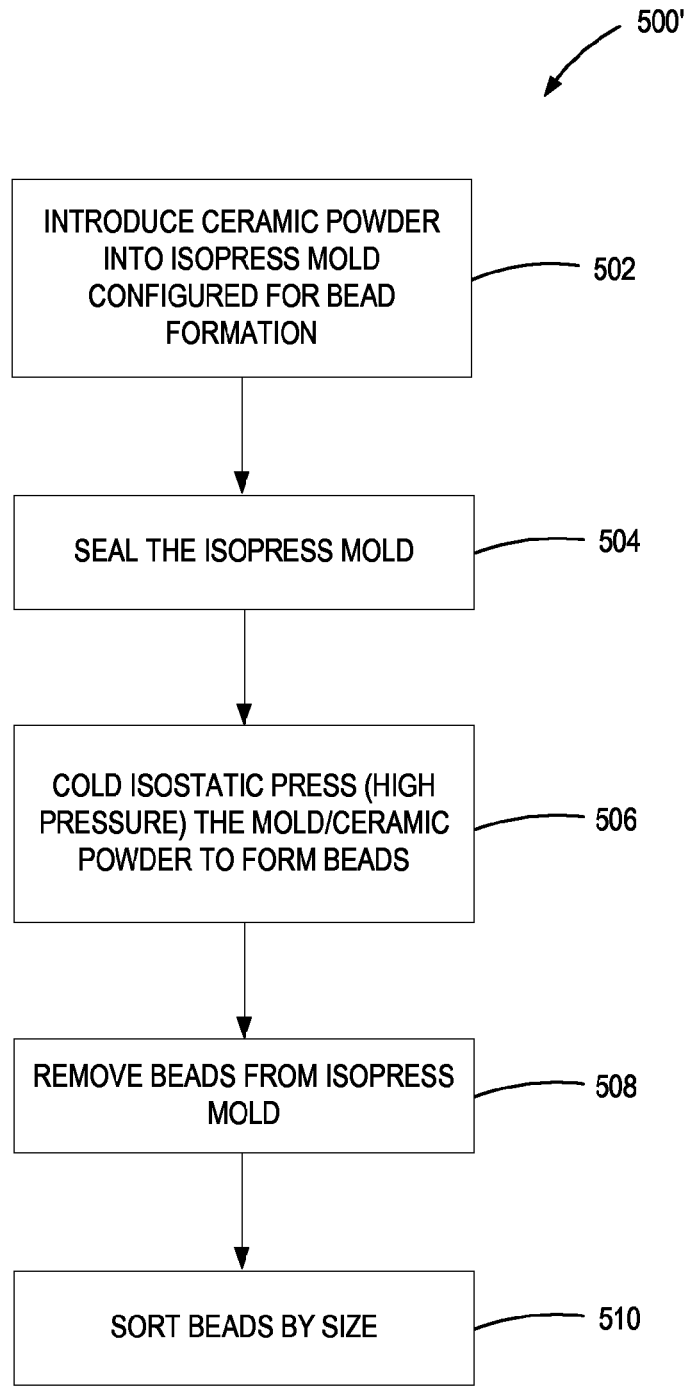
FIG. 30 is a flow chart that depicts another illustrative method of forming coating particles that can be mounted to a base piece, such as that shown in FIG. 5.

FIG. 30 depicts another method 500' for forming coating particles, which resembles the method 500. However, the method 500' includes an additional stage in which beads that are removed from the isopress mold are sorted according to size at stage 510. As discussed further below, in some embodiments, no such sorting is performed, since the isopress mold may be configured to create beads of only a single size, or may be configured only to create beads that are within a desired or specified size range.

Figure 31:
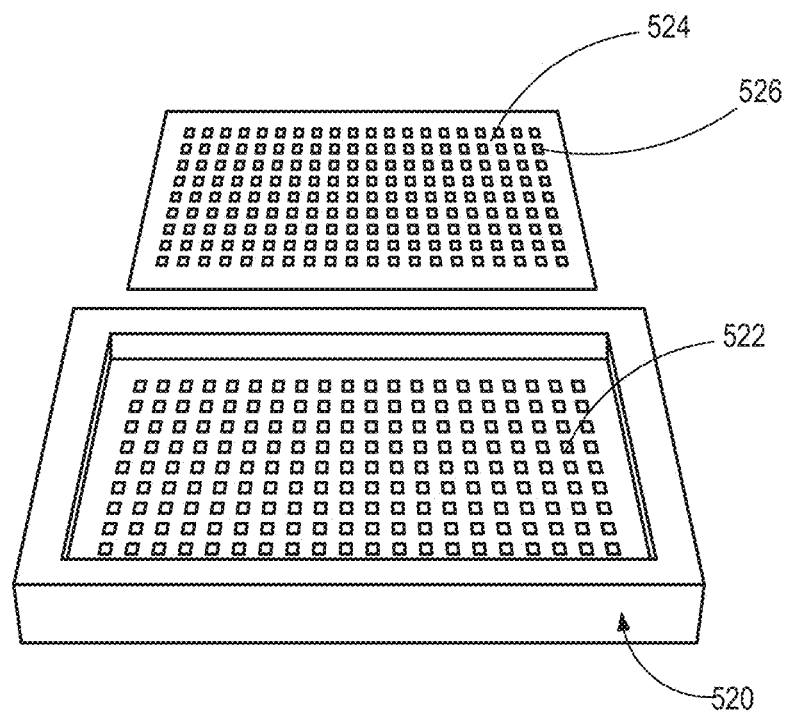
FIG. 31 is a perspective view of an isopress mold that is suitable for use with the methods of FIGS. 29 and 30.

FIG. 31 illustrates an embodiment of an isopress mold 520 that can be used with either of the methods 500, 500'. As the mold 520 is configured to prepare beads of a uniform size and shape, however, the mold 520 may be more particularly suited for the method 500 in which no sorting is performed after creation of the beads. The mold 520 defines a plurality of depressions or cavities 522 that are spherically shaped and are arranged in a series of rows and columns. Other shapes, sizes, and orientations of the cavities 522 are also possible. For example, similarly configured molds 520 may have larger cavities 522 in order to form larger beads. Although the illustrated embodiment is configured to form spherically shaped beads, it is noted that beads of any desired shape are possible (parallelepiped, ovoid, etc.).

FIG. 31 further illustrates an embodiment of mold 520 that comprises a top sheet 524 that may also be used in forming the isopress mold 520. The top sheet 524 may define a negative of the fill region of the isopress mold 520, and may comprise a series of spherically, or hemi-spherically shaped cavities 526 that are arranged in rows and columns and may be arranged to correspond with the rows and columns of cavities 522 such that both pieces when brought together form spherical particles. Methods for producing such a mold 520 are discussed further below.

In some embodiments, one of top sheet 524 and the mold 520, such as top sheet 524, may comprise a rigid material, such as a rigid plastic material. In such embodiments, the other of the two components, such as mold 520, may comprise a pliable material, such as a soft rubber, that may flex in order to provide for desirable compaction of the powders contained in the mold.

With continued reference to FIG. 31, ceramic powder can be introduced into the mold 520 and tightly packed into the cavities 522. In some embodiments, a vibratory plate or other vibration mechanism is used to tightly pack ceramic powder. A shallow layer of ceramic powder may also be included above the cavities 522. Once the ceramic powder is in place, the isopress mold 520 may be sealed in any suitable manner. For example, in some embodiments, the isopress mold 520 may be vacuum sealed (e.g., via a Seal-a-Meal® vacuum storage bag using a Seal-a-Meal® vacuum sealer available from Sunbeam Products, Inc.).

The mold 520 can be positioned in a cold isostatic press for stage 506. In various embodiments, pressures used for the CIP are within a range of from about 20,000 psi to about 66,000 psi; from about 25,000 psi to about 50,000 psi, or from about 30,000 psi to about 40,000 psi; the pressures are no greater than about 25,000; 30,000; 35,000; 40,000; 45,000; or 50,000 psi; or the pressures are no less than about 25,000; 30,000; 35,000; 40,000; 45,000; or 50,000 psi. In some embodiments, a pressure of about 33,155 psi is used. In various embodiments, a cold isostatic press that is rated at approximately 66,000 psi can be used for the CIP procedure.

Figure 32:
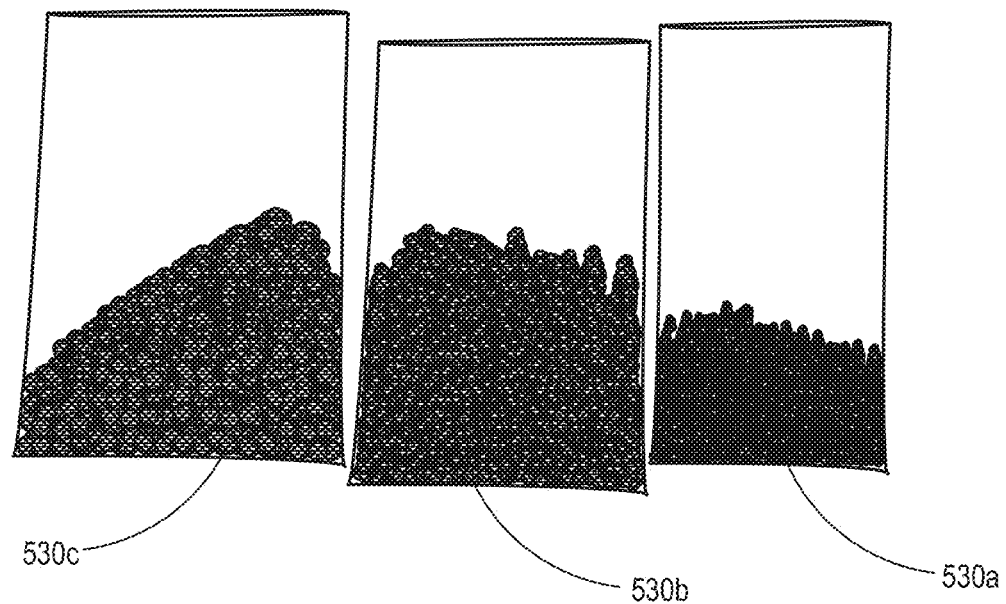
FIG. 32 is a perspective view of three bags that contain, respectively, coating particles of three different sizes, wherein the coating particles have been formed in accordance with either of the methods of FIGS. 29 and 30.

FIG. 32 shows three separate bags filled with coating particles (beads) 530*a*, 530*b*, 530*c* that were formed in accordance with either of the methods 500, 500'. In the illustrated embodiment, the beads 530*a*, 530*b*, 530*c* have diameters that are somewhat less than about 1.3 millimeters, about 2.4 millimeters, and about 3.2 millimeters, respectively. Other sizes for the beads 530 are also possible. For example, in various embodiments, the beads 530 may be within a range of from about 0.5 millimeters to about 4 millimeters, from about 1 millimeter to about 3 millimeters, or from about 1.5 millimeters to about 2.5 millimeters, when in the green state.

Beads 530 of a single size or of multiple sizes may be introduced into an isopress mold with a partially compacted inner cup 13 in any suitable manner. The beads 530 may also be pressed into the outer surface of the inner cup 13. Accordingly, the beads 530, or coating particles, may be attached to the cup 13 in a manner such as discussed above with respect to method 180 (FIG. 9).

Figure 33:
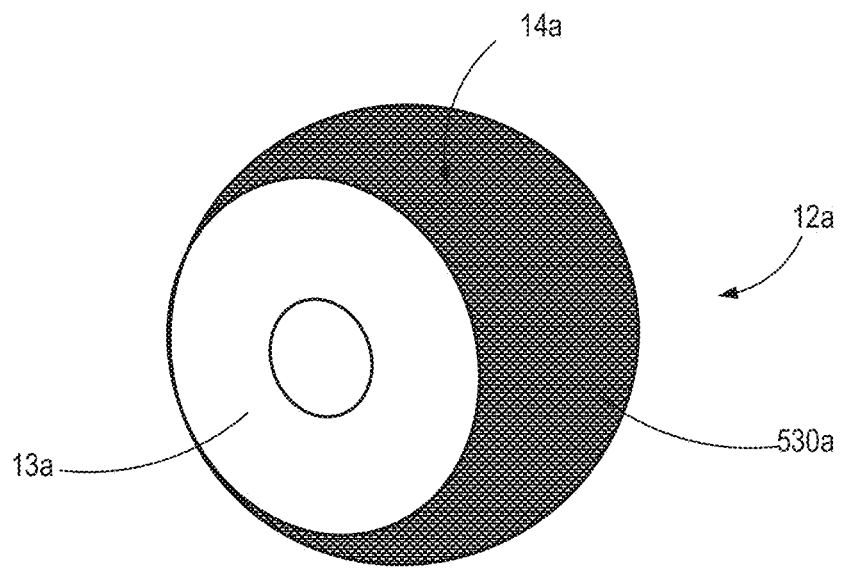
FIG. 33 is a perspective view of an embodiment of a multi-layer ceramic part that has been formed in accordance with the method of FIG. 13 and either of the methods of FIGS. 29 and 30.

FIG. 33 shows a perspective view of a ceramic device 12*a* in a green state that was formed in accordance with methods 200, 102, 500 (or 500'), and 180 of FIG. 13, 3, 29 (or 30), and 9, respectively, using the beads 530*a* of FIG. 32. Although the ceramic device 12*a* depicted in FIG. 33 is depicted with a relatively small central opening, those of ordinary skill will appreciate that the principles used in the formation of this device may, for certain embodiments, be more useful for components that will interface with a patient's bone such as an acetabular cup for a hip implant. As such, the central opening may be expanded and shaped to fit with a corresponding femoral implant in some embodiments.

Figure 34:
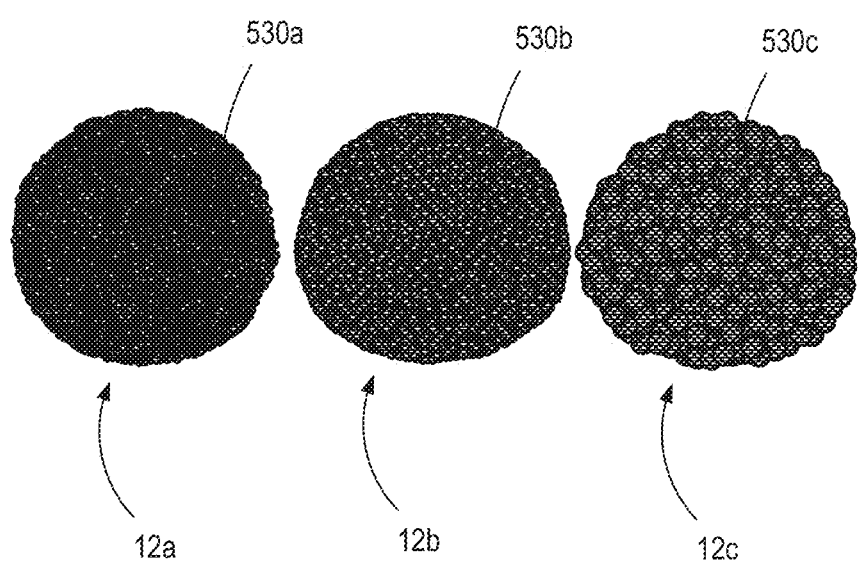
FIG. 34 is a perspective view of three different embodiments of multi-layer ceramic parts that have been formed in accordance with the method of FIG. 13 and either of the methods of FIGS. 29 and 30, wherein the coating particles that form an outer layer of the ceramic part are progressively larger, and wherein the multi-layer parts are shown in a green state.
Figure 36A:
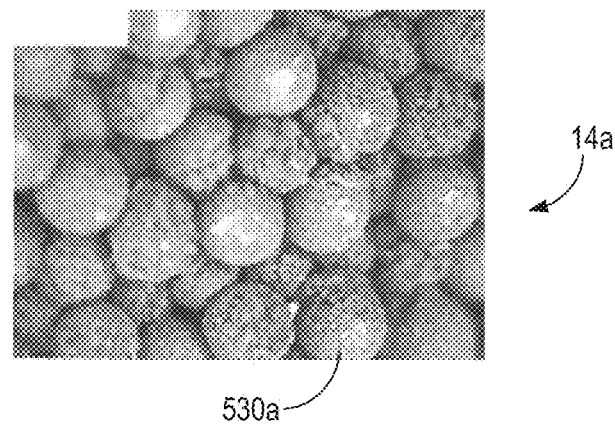
FIG. 36A is a stereomicroscope photograph of the outer layer of the multi-layer part at the left in FIG. 35, wherein the scale depicted in the insert at the upper left-hand corner of the photograph defines a length of 1000 µm.
Figure 36B:
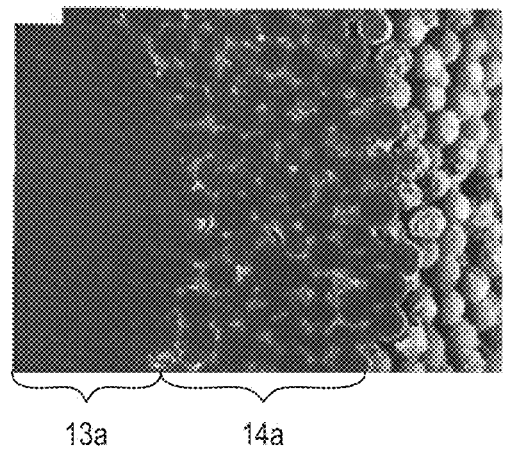
FIG. 36B is a stereomicroscope photograph of a cross-section of the multi-layer part at the left in FIG. 35, wherein the scale depicted in the insert at the upper left-hand corner of the photograph defines a length of 1000 µm.
Figure 36C:
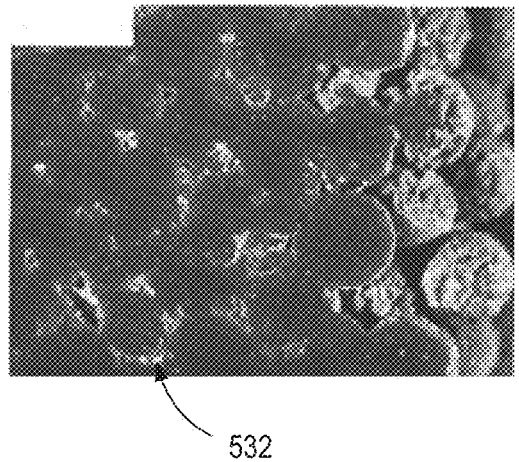
FIG. 36C is a stereomicroscope photograph of a cross-section of the mutli-layer part at the left in FIG. 35, wherein the scale depicted in the insert at the upper left-hand corner of the photograph defines a length of 1000 µm.
Figure 37A:
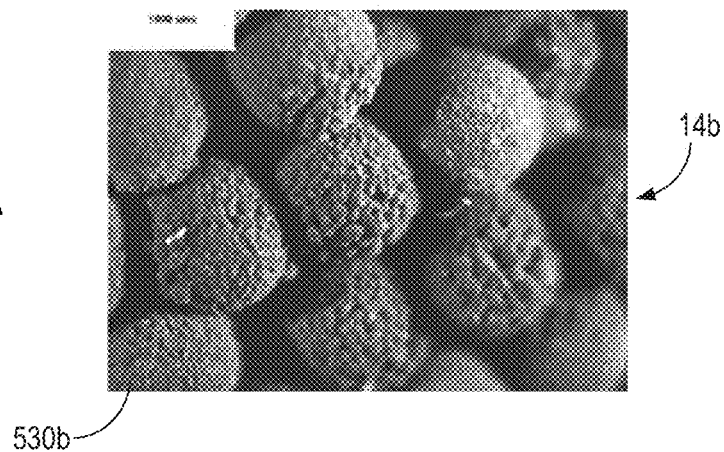
FIG. 37A is a stereomicroscope photograph of the outer layer of the multi-layer part at the center in FIG. 35, wherein the scale depicted in the insert at the upper left-hand corner of the photograph defines a length of 1000 µm.
Figure 37B:
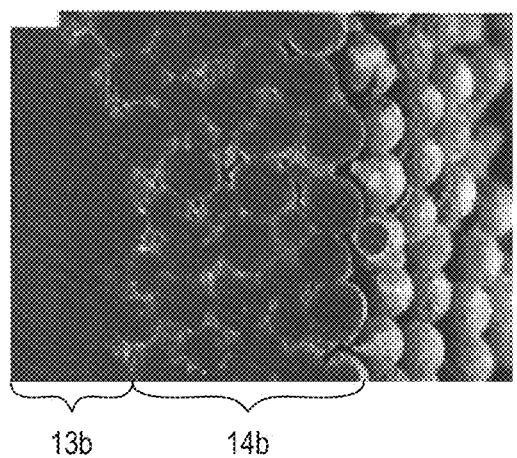
FIG. 37B is a stereomicroscope photograph of a cross-section of the multi-layer part at the center in FIG. 35, wherein the scale depicted in the insert at the upper left-hand corner of the photograph defines a length of 1000 µm.
Figure 37C:
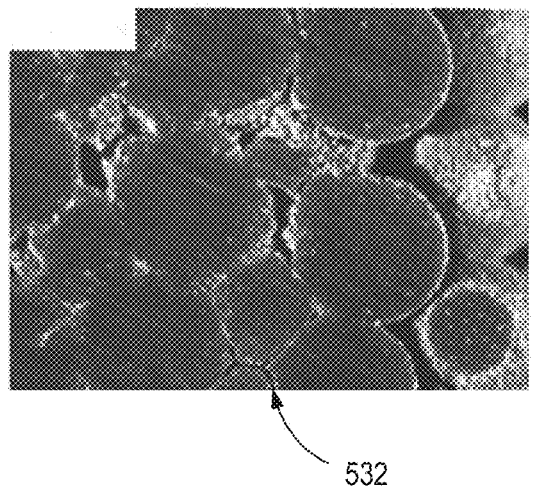
FIG. 37C is a stereomicroscope photograph of a cross-section of the multi-layer part at the center in FIG. 35, wherein the scale depicted in the insert at the upper left-hand corner of the photograph defines a length of 1000 µm.
Figure 38A:
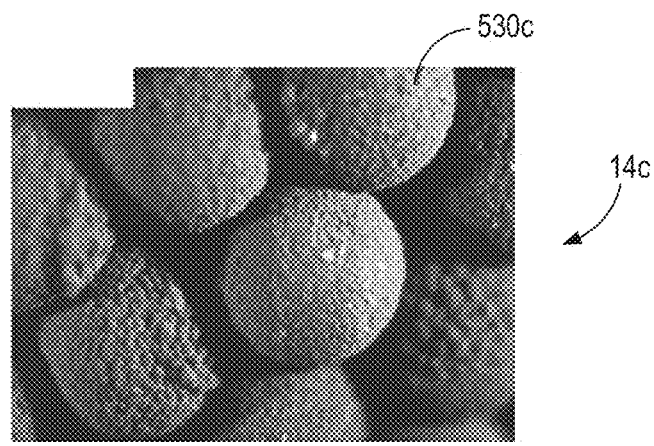
FIG. 38A is a stereomicroscope photograph of the outer layer of the multi-layer part at the right in FIG. 35, wherein the scale depicted in the insert at the upper left-hand corner of the photograph defines a length of 1000 µm.
Figure 38B:
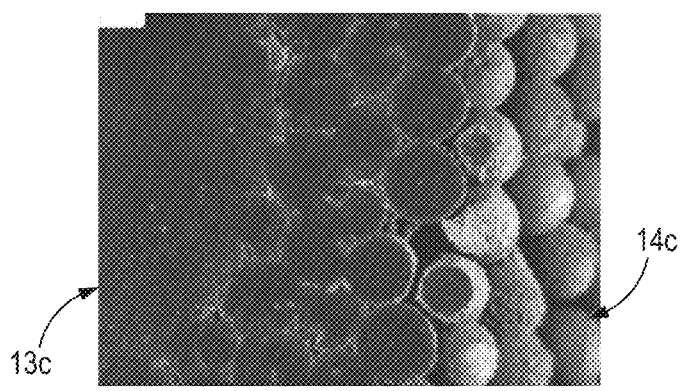
FIG. 38B is a stereomicroscope photograph of a cross-section of the multi-layer part at the right in FIG. 35, wherein the scale depicted in the insert at the upper left-hand corner of the photograph defines a length of 1000 µm.
Figure 38C:
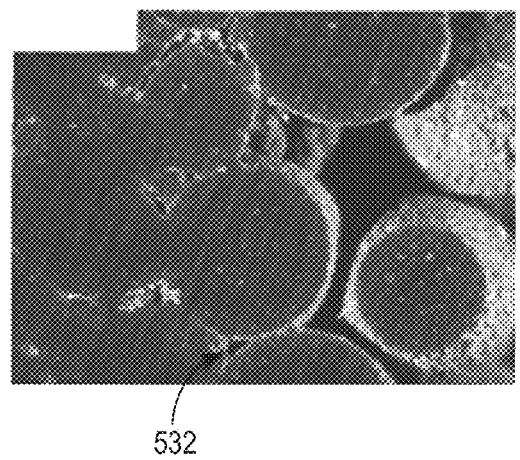
FIG. 38C is a stereomicroscope photograph of a cross-section of the mutli-layer part at the right in FIG. 35, wherein the scale depicted in the insert at the upper left-hand corner of the photograph defines a length of 1000 µm.

FIG. 34 shows a different perspective view of the ceramic device 12*a*, as well as ceramic devices 12*b*, 12*c* that are in a green state and were formed with the beads 530*a*, 530*b*, 530*c*, respectively. FIG. 35 shows a perspective view of the ceramic devices 12*a*, 12*b*, 12*c* after having been fired. FIGS. 36A-36C, 37A-37C, and 38A-38C illustrate various views of the ceramic devices 12*a*, 12*b*, 12*c* of FIG. 34, which views are similar to those depicted in FIGS. 19A-19C, 20A-20C, and 21A-21C for the implant parts 12*a*, 12*b*, 12*c* of FIG. 18. Pores within the outer layers 14*a*, 14*b*, 14*c* are identified at reference numeral 532 (see FIG. 36C). The outer layers 14*a*, 14*b*, 14*c* can have excellent fusion interfaces with the inner cups 13*a*, 13*b*, 13*c*. As with the implants shown in FIGS. 17A-17C, it should be understood that the devices shown in these figures are provided for purposes of illustration, and it may be more likely that such devices would instead be constructed with the most porous layers positioned in alternative positions on the device, such as only on one side of the device.

Figure 39:
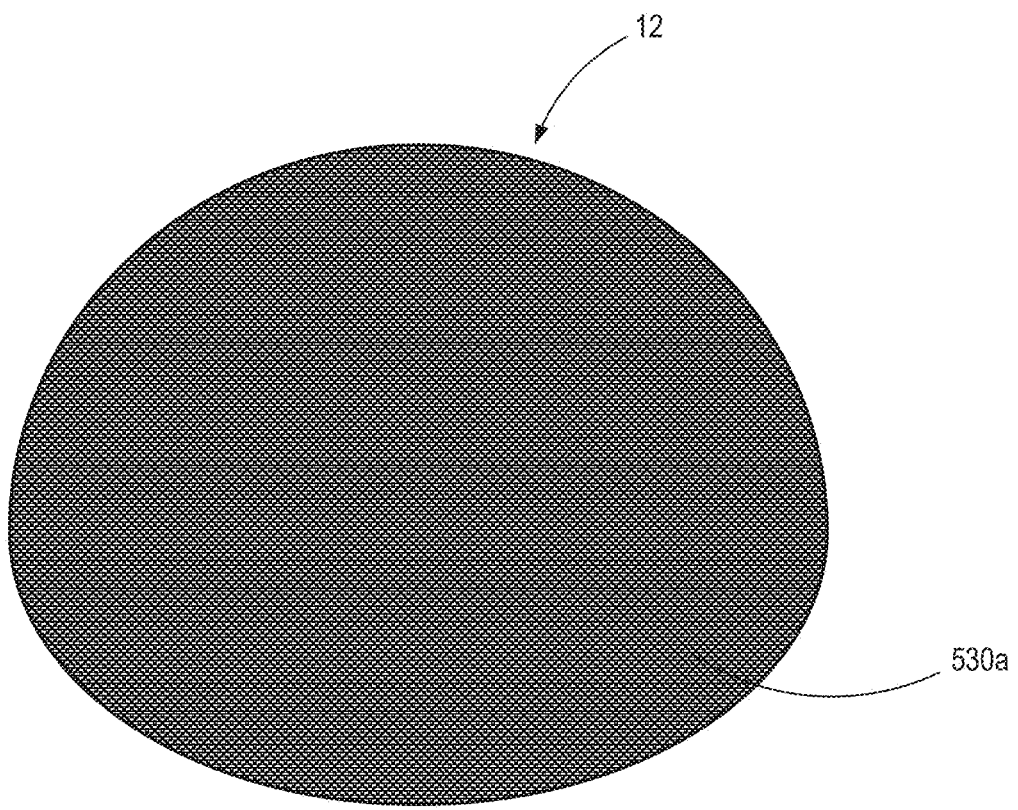
FIG. 39 is a perspective view of another embodiment of a multi-layer part that has been formed in accordance with the method of FIG. 13 and either of the methods in FIGS. 29 and 30.

FIG. 39 shows a perspective view of another embodiment of a monoblock cup 12 in a green state that was formed using the small beads 530*a* of FIG. 32. The cup 12 was formed using the isopress tooling 130 of FIG. 4, and thus is substantially hemispherical.

Figure 40A:
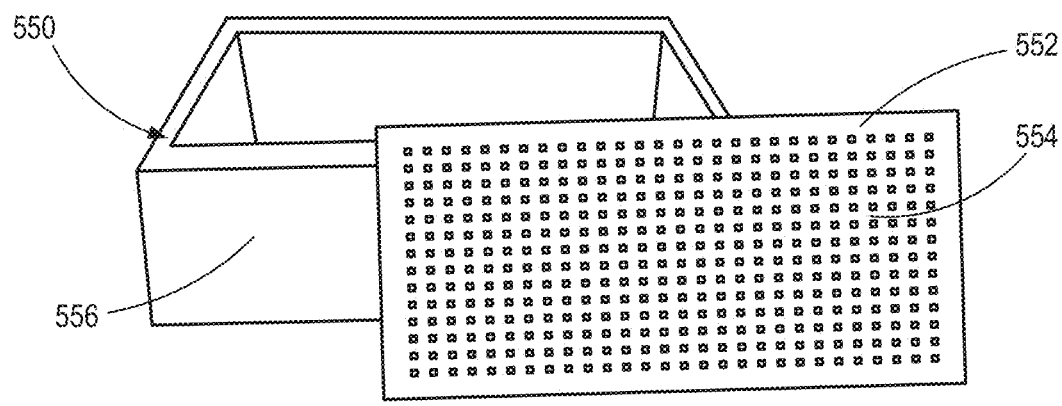
FIGS. 40A and 40B are perspective views of an embodiment of a template and an embodiment of an isopress mold formed thereby, respectively, wherein the isopress mold is configured for use with either of the methods of FIGS. 29 and 30.
Figure 40B:
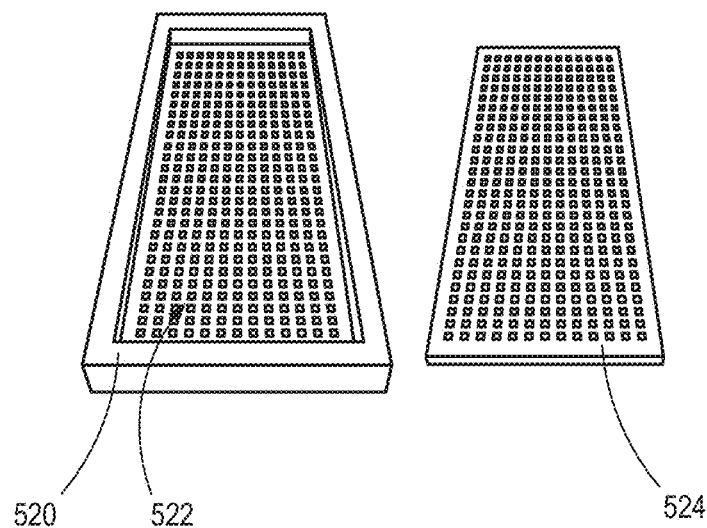

FIG. 40A is a perspective view of a master mold 550 that was used to create the isopress mold 520, which is also shown in FIG. 40B. The master mold 550 includes an aluminum receptacle 556 that is sized to receive an aluminum plate 552 therein. A plurality of stainless steel ball bearings 554 are bonded to an underside of the aluminum plate 552. The ball bearings 554 are used to form the cavities 522. The ball bearings 554 can be of any desired size. For embodiments such as those depicted in FIGS. 33-39, the ball bearings 554 can have diameters of about 1.3 millimeters, about 2.4 millimeters, and about 3.2 millimeters. The master mold 550 can be back cast out of silicone and polyurethane and/or any other suitable material to form the isopress mold 520.

Figure 41:
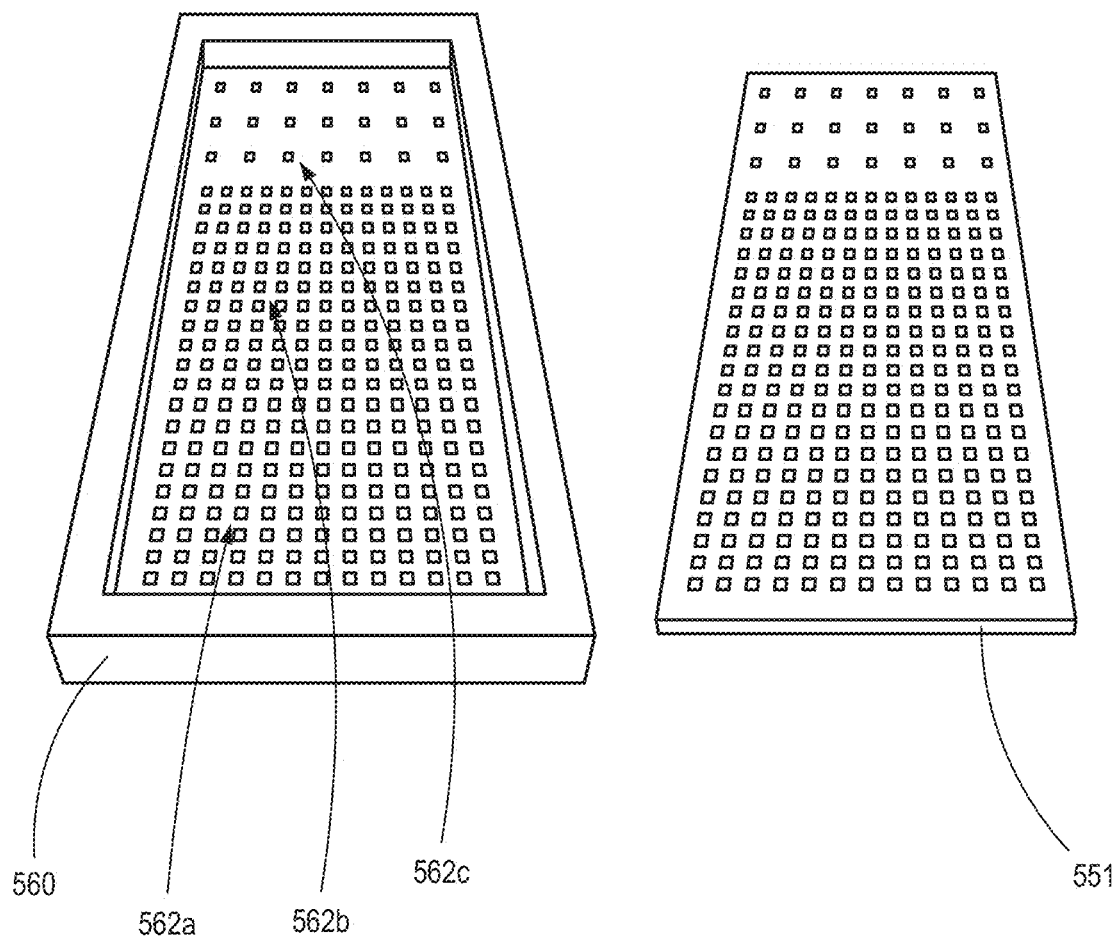
FIG. 41 is a perspective view of another embodiment of an isopress mold configured for use with either of the methods of FIGS. 29 and 30.

FIG. 41 shows another embodiment of an isopress mold 560 that includes depressions 562*a*, 562*b*, 562*c* of different sizes. The mold 560 can be used to fabricate multiple sizes of coating particles 530 simultaneously. Accordingly, where only a single size of coating particle 530 is desired for a particular monoblock cup 12, the method 500', which includes a step for sorting beads by size, may desirably be used.

Figure 42A:
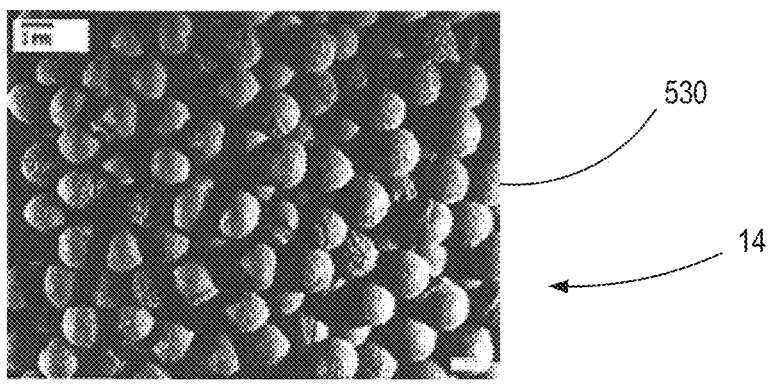
FIGS. 42A-42C are perspective views of outer layers of multi-layer parts that have been formed in accordance with an example of either the method of FIG. 29 or the method of FIG. 30, as well as the method of FIG. 13 (for FIG. 42A); the method of FIG. 14, as well as the method of FIG. 30 (for FIG. 42B); and either the method of FIG. 22 or the method of FIG. 23, as well as the method of FIG. 30 (for FIG. 42C), which are shown for discussion regarding the relative porosities of the different configurations, wherein the scale depicted in the insert at the upper left-hand corner of each of FIGS. 42A-42C defines a length of 1000 µm.
Figure 42B:
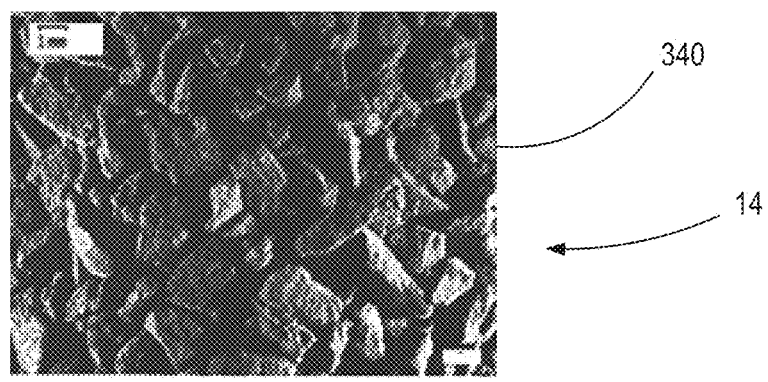
Figure 42C:
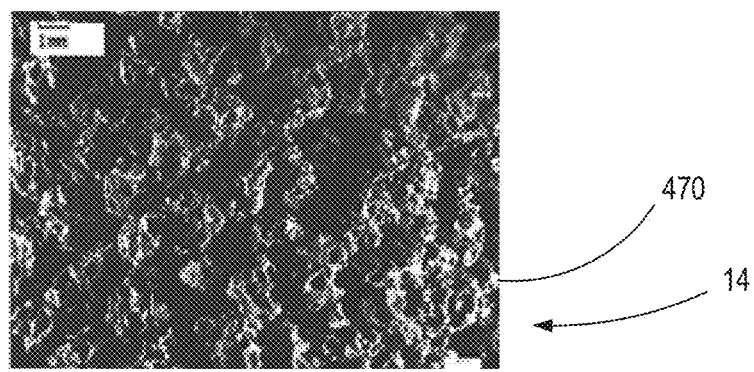

FIGS. 42A, 42B, 42C show three different outer layers 14 that include coating particles 530, 340, 470 that were formed in accordance with the methods 500, 300, 400, respectively. The illustrated layers 14 have estimated porosities of approximately 33.8 percent, 42.1 percent, and 56.2 percent, respectively. As can be appreciated from the foregoing, different arrangements of the outer layer 14 can be achieved by altering the properties (e.g., size, shape, etc.) and/or types (e.g., chips, coated pore formers, beads, etc.) of coating particles used. In various embodiments the outer layer 14 can have a porosity that is within a range of from about 20 percent to about 80 percent, from about 45 percent to about 65 percent, or from about 50 percent to about 60 percent, that is no less than about 20, 30, 40, 45, 50, 55, 60, or 65 percent, or that is no greater than about 40, 50, 60, 70, or 80 percent. Porosity can be determined via any suitable test or technique, including, for example, planar porosity evaluations, dimensional porosity evaluations, and/or mercury intrusion porosimetry. If desired, pore size may be determined by such methods as modified grain size measurements, such as by treating pores as grains while using ASTM grain size measurements via, for example, an interception method.

The outer layers 14 may be tested for other properties, such as bulk strength. An example of a test that may be used to test this property is a standard compression/impaction test. Another property that may be tested is the abrasion resistance, which can be achieved via the Taber abrasion test. Yet another property that may be tested, and which may distinguish the various outer layers 14 from each other, is bone ongrowth capability (which may be conducted clinically).

The methods provided herein can be altered or modified so as to provide the monoblock cups 12 with additional attachment features. For example, in some embodiments, the monoblock cups 12 may include grooves, spirals (e.g., threads), or alternating patches of dense and porous sections. Such features may be used during insertion of the monoblock cup 12 into the pelvis. In other or further embodiments, the monoblock cups 12 can include holes for screws or other attachment hardware. In some embodiments, these features may be formed in the monoblock cups 12 during CIP processes, or they may be machined into the monoblock cups 12 thereafter, whether in the green state or in the fired state.

Figure 43:
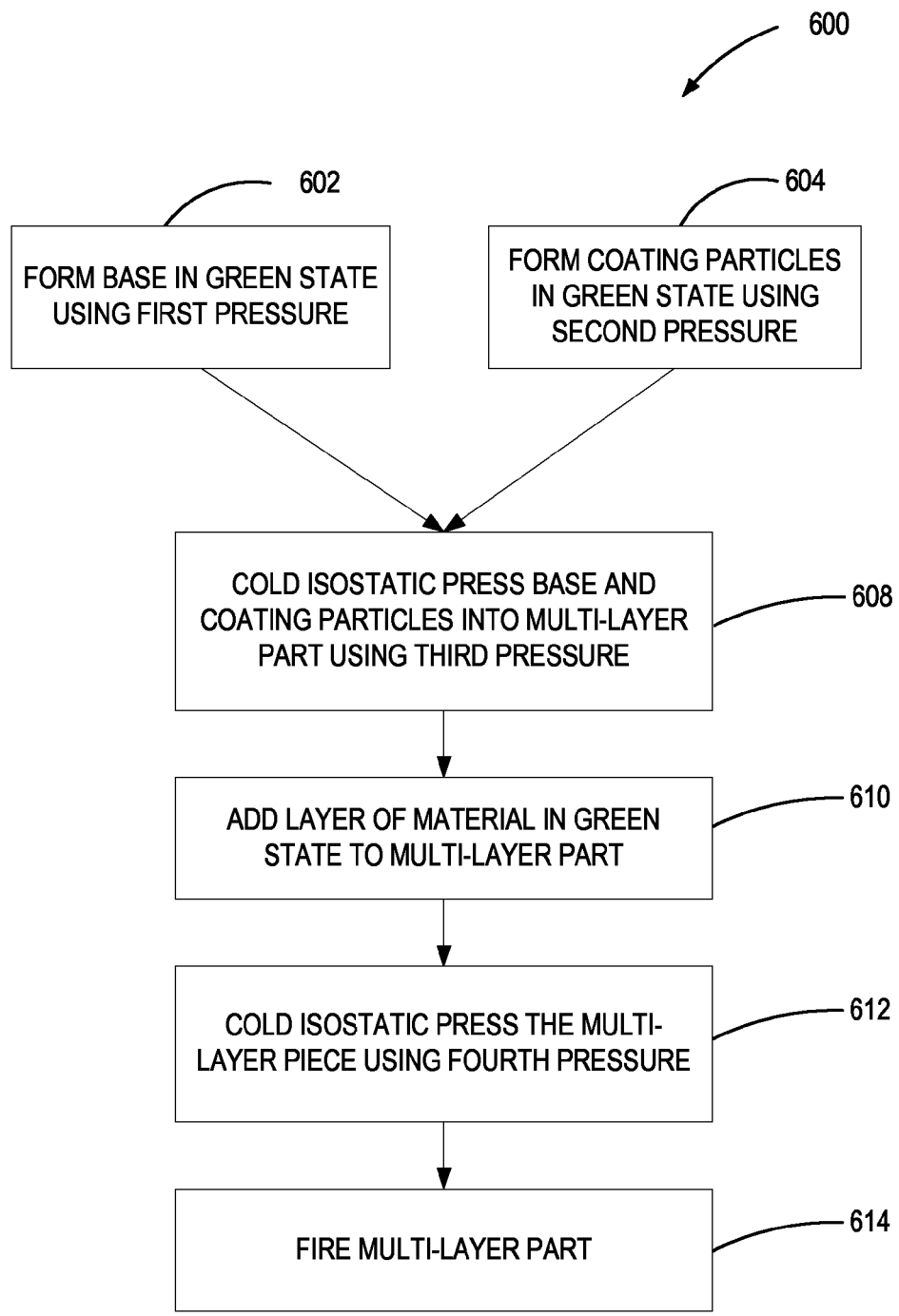
FIG. 43 is a flow chart that depicts another illustrative method of forming a multi-layer ceramic part, such as the acetabular cup of FIG. 1B, that has a variable density.

FIG. 43 depicts another illustrative method 600 for manufacturing a multi-layer ceramic part, such as the monoblock cup 12 discussed above. The method 600 is similar to the method 200, and the stages 602, 604, 608, 614 may be identical to stages 202, 204, 208, 210, respectively, discussed above. The method 600 further includes a stage 610 in which an additional layer of ceramic material in a green state is added to the multi-part layer that is formed in stage 608. In some embodiments, the additional layer of ceramic material can include additional coating particles that were formed during stage 604 using the second pressure. In other or further embodiments, the additional layer of ceramic material can include coating particles that were formed in a different stage. For example, the coating particles can be formed using the method 104 described above. In other embodiments, the coating particles can be formed at a pressure that is different from the second pressure of stage 604. At stage 612, the multi-layer part, which now includes yet another layer, is cold isostatic pressed using a fourth pressure to compact the multi-layer part into a monolithic piece. Accordingly, the final multi-part may include three layers, which may each have different densities or porosities. As can be appreciated from the foregoing, stages 608, 610 may be repeated as many times as desired and/or practicable, at additional pressures, to create additional layers. The first, second, third, and fourth pressures, and any additional pressures, can be adjusted as desired to form layers and interfaces having the desired properties. Accordingly, various embodiments can employ dual-isopressing or multi-isopressing processes.

Figure 44:
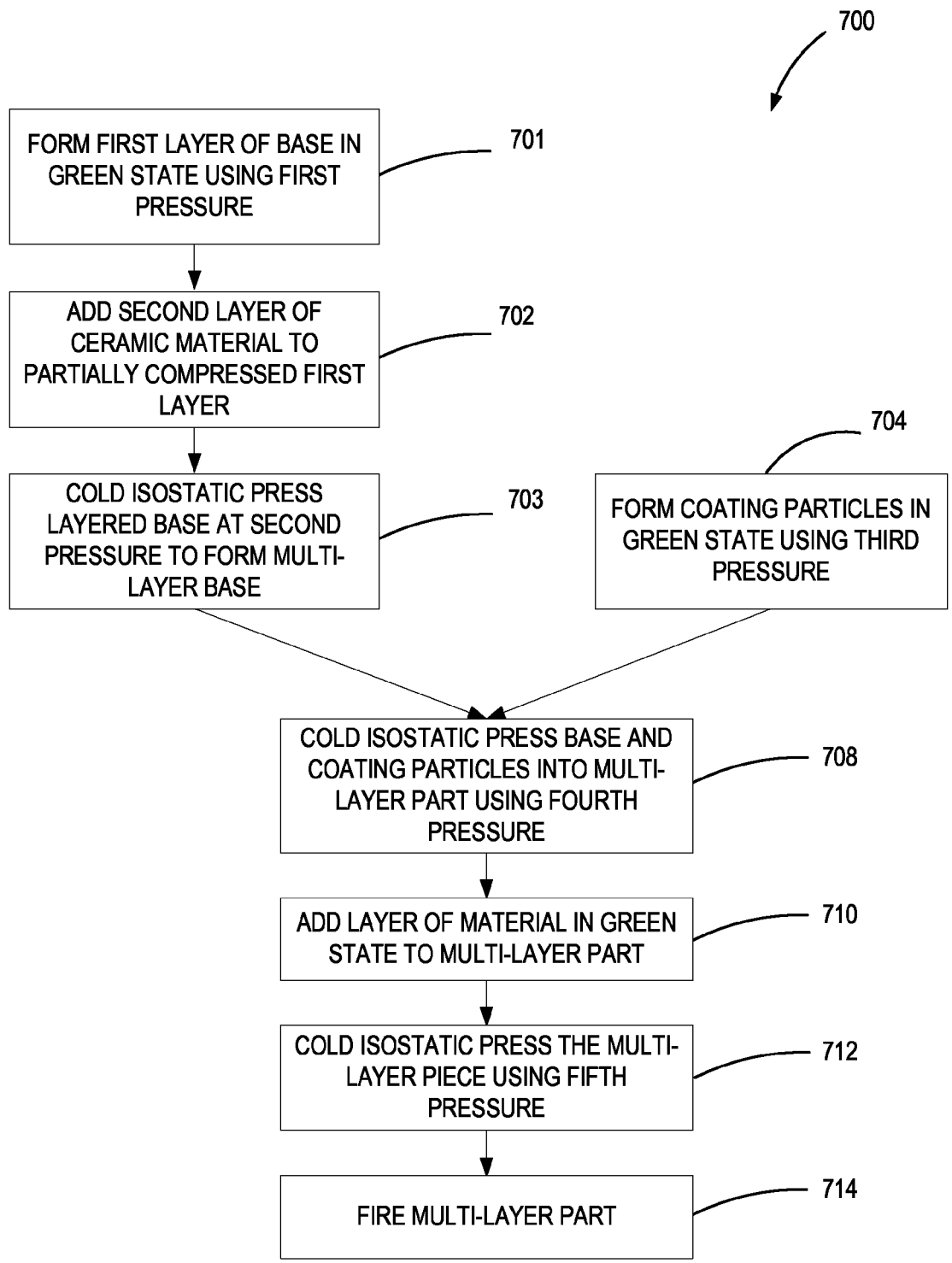
FIG. 44 is a flow chart that depicts another illustrative method of forming a multi-layer ceramic part, such as the acetabular cup of FIG. 1B, that has a variable density.

FIG. 44 depicts another illustrative method 700 for manufacturing a multi-layer ceramic part, such as the monoblock cup 12 discussed above. The method 700 is similar to method 200. However, in method 700, a mutli-layer base is formed, and one or more layers of coating particles are added to the multi-layer base. In particular, at stage 701, a first layer of a base is formed in a green state using a first pressure, similar to stage 602 of the method 600. The first layer of the base is thus partially compressed. At stage 702, a second layer of ceramic material is added to the first layer of the base. The ceramic material may be the same as or different from the ceramic material of the first layer. In some embodiments, an isopress mold (e.g., the isopress mold 140 of FIG. 4) can be backfilled with ceramic powder, which may be achieved using a vibration plate.

At stage 703, the first and second layers are compressed together using cold isostatic pressing at a second pressure. The second pressure may be less than, greater than, or about the same as the first pressure, depending on the desired result. Stage 703 yields a multi-layer base. The layers may have different compositions, densities, and/or other properties. As can be appreciated from the foregoing, the stages 702, 703 may be repeated as many times as desired and/or practicable, at additional pressures, to create additional layers.

Stages 704, 708, 710, 712, and 714 resemble stages 604, 608, 610, 612, and 614, respectively discussed above. In some embodiments, stages 710 and 712 may be skipped. Accordingly, the final multi-part may include three or more layers or four or more layers, any of which may have different densities, porosities, or other properties. The first, second, third, fourth, and/or fifth pressures, and any additional pressures, can be adjusted as desired to form layers and interfaces having the desired properties.

Figure 45:
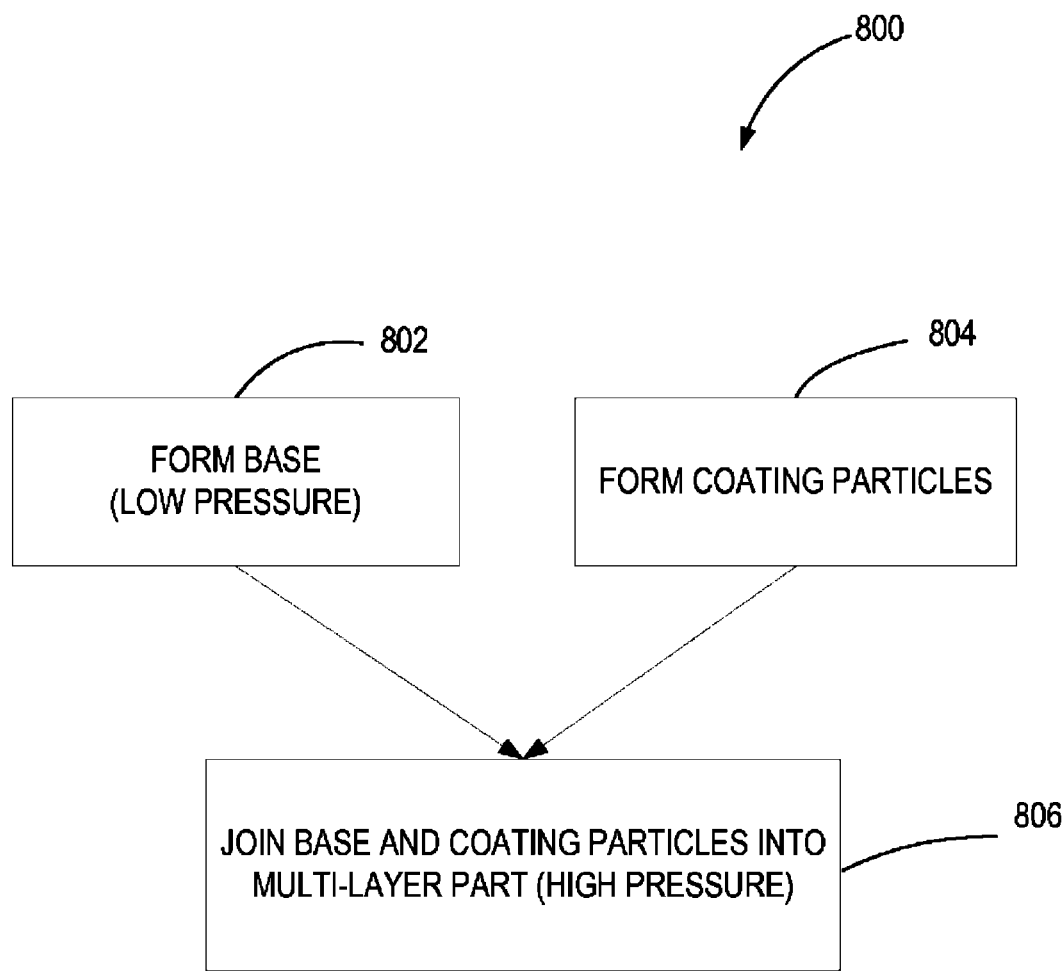
FIG. 45 is a flow chart that depicts another illustrative method of forming a multi-layer ceramic part, such as the acetabular cup of FIG. 1B, that has a variable density.

FIG. 45 depicts another illustrative method 800 for manufacturing a multi-layer ceramic part, such as the monoblock cup 12 discussed above. At stage 802, a ceramic base, such as the inner cup 13, is formed at a low pressure. At stage 804, coating particles are formed in any suitable manner, such as via any of the methods discussed above. At stage 806, the base 13 and the coating particles are joined to each other to form a multi-layer part, such as the monoblock cup 12. Stage 802 may preferably use CIP to form a partially compacted base 13. Similarly, stage 806 may also use CIP (as discussed in other methods above) to join the base 13 and the coating particles.

Although the specific examples mentioned above and discussed in the accompanying documents are directed to the formation of acetabular cups, other devices, whether ceramic or otherwise, may also be formed via these methods. Such devices can include, for example, other orthopedic implants, dental or other oral implants, and other medical devices, such as other orthopedic implants, including shoulder joint implants, femoral condyles, and tibial trays.

Any methods disclosed herein comprise one or more steps or actions for performing the described method. The method steps and/or actions may be interchanged with one another, where appropriate. In other words, unless a specific order of steps or actions is required for proper operation of the embodiment, the order and/or use of specific steps and/or actions may be modified.

References to approximations are made throughout this specification, such as by use of one or more of the terms "about," "approximately," "substantially," and "generally." For each such reference, it is to be understood that, in some embodiments, the value, feature, or characteristic may be specified without approximation. For example, where such a qualifier is used, the term includes within its scope the qualified word in the absence of the qualifier.

Unless otherwise noted, the terms "a" or "an" are to be construed as meaning "at least one of." In addition, for ease of use, the words "including" and "having" are interchangeable with and have the same meaning as the word "comprising." Recitation of the term "first" with respect to a feature or element does not necessarily imply the existence of a second or additional such feature or element.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

It will be apparent to those having skill in the art that changes may be made to the details of the above-described embodiments without departing from the underlying principles set forth herein. The scope of the present invention should, therefore, be determined only by the following claims.

The invention claimed is:

1. A method for manufacturing a silicon nitride ceramic hip prosthesis, the method comprising the steps of:
    performing a first isopressing process to form a base portion of a monolithic acetabular cup, wherein the base portion comprises a silicon nitride ceramic material at a first density;
    performing a second isopressing process to form coating particles comprising a silicon nitride ceramic material;
    combining the coating particles with the base portion in an isopress mold;
    performing a third isopressing process on the combined base portion and coating particles to form a first layer of silicon nitride ceramic made up of the coating particles on the base portion, wherein the first layer comprises a second density, and wherein the second density is less than the first density; and
    firing the combined base portion and coating particles to form a monolithic acetabular cup for a hip prosthesis.

2. The method of claim 1, further comprising performing a fourth isopressing process to form a second set of coating particles, wherein the second set of coating particles comprise a silicon nitride ceramic material.

3. The method of claim 2, wherein the fourth isopressing process is performed before the third isopressing process.

4. The method of claim 2, further comprising combining the second set of coating particles with the base portion and the coating particles.

5. The method of claim 4, further comprising performing a fifth isopressing process on the combined base portion, coating particles, and second set of coating particles to form a third layer of silicon nitride ceramic made up of the second set of coating particles, wherein the third layer comprises a third density, and wherein the third density is less than the second density.

6. The method of claim 1, wherein the step of performing a third isopressing process comprises performing the third isopressing process on the base portion, the coating particles, and a second set of coating particles to form the first layer of silicon nitride ceramic made up of the coating particles on the base portion and a second layer of silicon nitride ceramic made up of the second set of coating particles on the first layer, wherein the second layer comprises a third density, and wherein the third density is less than the second density.

7. The method of claim 1, wherein the coating particles comprise silicon nitride ceramic chips.

8. The method of claim 1, wherein the coating particles comprise spherical silicon nitride beads.

9. The method of claim 1, wherein the coating particles comprise pore former cores coated with silicon nitride material, wherein the pore former cores are configured to form pores in the silicon nitride material upon firing.

10. A method for manufacturing a ceramic biomedical implant, the method comprising the steps of:
    coating a first set of particles with a silicon nitride ceramic powder to form a first set of coated particles, wherein the first set of particles comprise pore former cores configured to form pores in a silicon nitride ceramic material upon firing;
    performing a first isopressing process to form a base of a ceramic biomedical implant, wherein the base comprises a first density;
    applying the first set of coated particles to at least a portion of the base;
    performing a second isopressing process on the base with the first set of coated particles to form a first layer, wherein the first layer comprises a second density, and wherein the second density is less than the first density; and
    firing the base and the first set of coated particles together to form a ceramic biomedical implant, wherein the step of firing the base and the first set of coated particles together causes the pore former cores to form pores in the first layer.

11. The method of claim 10, wherein the pore former cores comprise at least one of polyethylene wax, microcrystalline cellulose, naphthalene, polyethylene glycol, and urea.

12. The method of claim 10, further comprising:
    coating a second set of particles with a silicon nitride ceramic powder to form a second set of coated particles, wherein the second set of particles comprise pore former cores configured to form pores in a silicon nitride ceramic material upon firing;
    applying the second set of coated particles to at least a portion of the first layer; and
    performing a third isopressing process on the base with the second set of coated particles to form a second layer, wherein the second layer comprises a third density, and wherein the third density is less than the second density.

13. The method of claim 12, wherein the second set of particles have a larger maximum diameter than the first set of particles such that the second layer is formed with pores having a larger average volume than the pores in the first layer.

14. The method of claim 10, wherein the base portion comprises a silicon nitride ceramic material.

15. The method of claim 10, further comprising performing a third isopressing process to form the first set of coating particles, and wherein the step of performing a third isopressing process is performed before the step of performing a second isopressing process.

16. The method of claim 10, further comprising sorting the first set of particles by size such that the first set of particles comprises only particles having a diameter less than a threshold diameter.

17. The method of claim 10, further comprising sorting the first set of coated particles by size after the step of coating the first set of particles with a silicon nitride ceramic powder such that the first set of coated particles comprises only coated particles having a diameter less than a threshold diameter.

* * * * *